US011360084B2

(12) United States Patent
Deutsch et al.

(10) Patent No.: US 11,360,084 B2
(45) Date of Patent: Jun. 14, 2022

(54) METHODS AND APPARATUS FOR DETECTING ANALYTES

(71) Applicant: SALIGNOSTICS LTD., Jerusalem (IL)

(72) Inventors: Omer Deutsch, Ofra (IL); Raluca Cohen, Jerusalem (IL); Yoav Neumann, Tzur Hadassah (IL); Guy Krief, Jerusalem (IL)

(73) Assignee: SALIGNOSTICS LTD, Jerusalem (IL)

( * ) Notice: Subject to any disclaimer, the term of this patent is extended or adjusted under 35 U.S.C. 154(b) by 0 days.

(21) Appl. No.: 16/969,832

(22) PCT Filed: Feb. 13, 2019

(86) PCT No.: PCT/IL2019/050171
§ 371 (c)(1),
(2) Date: Aug. 13, 2020

(87) PCT Pub. No.: WO2019/159167
PCT Pub. Date: Aug. 22, 2019

(65) Prior Publication Data
US 2020/0386752 A1 Dec. 10, 2020

Related U.S. Application Data

(60) Provisional application No. 62/630,516, filed on Feb. 14, 2018.

(51) Int. Cl.
*G01N 33/543* (2006.01)
*G01N 33/558* (2006.01)
(Continued)

(52) U.S. Cl.
CPC ... *G01N 33/54386* (2013.01); *A61B 10/0051* (2013.01); *G01N 1/28* (2013.01);
(Continued)

(58) Field of Classification Search
CPC ....... G01N 33/54386; G01N 33/54306; G01N 33/558; G01N 33/56911; G01N 33/56961;
(Continued)

(56) References Cited

U.S. PATENT DOCUMENTS 5,339,829 A 8/1994 Thieme et al.
5,352,410 A * 10/1994 Hansen ................ A61B 10/007
422/419
(Continued)

FOREIGN PATENT DOCUMENTS

CN 105985950 A 10/2016
EP 0 616 650 B1 10/1998
(Continued)

OTHER PUBLICATIONS

International Preliminary Report on Patentability PCT/IL2019/050171 dated Feb. 19, 2020 (PCT/IPEA/409).
(Continued)

*Primary Examiner* — Robert J Eom
(74) *Attorney, Agent, or Firm* — Sughrue Mion, PLLC

(57) ABSTRACT

A barrel defines a channel, and has an opening into the channel, and an outlet from the channel. A porous carrier disposed within the channel carries an albumin. A cellulosic stationary phase is disposed within the channel between the carrier and the distal region of the barrel. A lateral flow platform is coupled to the barrel such that a sample pad of the lateral flow platform is in fluid communication with the outlet. A sponge, coupled to a plunger, is configured to hold saliva. The plunger is dimensioned to compress the sponge within the channel such that the saliva is driven (i) out of the sponge and through the carrier, dissolving at least some of the albumin, (ii) with the dissolved albumin, into the stationary phase, and (iii) as an eluate, out of the stationary
(Continued)

phase, through the outlet, and onto the sample pad. Other embodiments are also described.

42 Claims, 11 Drawing Sheets

(51) Int. Cl.
G01N 33/569 (2006.01)
G01N 1/40 (2006.01)
G01N 1/28 (2006.01)
A61B 10/00 (2006.01)

(52) U.S. Cl.
CPC .............. *G01N 1/286* (2013.01); *G01N 1/405* (2013.01); *G01N 33/54306* (2013.01); *G01N 33/558* (2013.01); *G01N 33/56911* (2013.01); *G01N 33/56961* (2013.01); *G01N 1/4044* (2013.01); *G01N 2001/2826* (2013.01)

(58) Field of Classification Search
CPC .......... G01N 1/28; G01N 1/286; G01N 1/406; G01N 1/4044; G01N 2001/2826; A61B 10/0051
See application file for complete search history.

(56) References Cited

U.S. PATENT DOCUMENTS

| | | | |
|---|---|---|---|
| 6,303,081 B1 | 10/2001 | Mink et al. | |
| 6,309,827 B1 | 10/2001 | Goldstein et al. | |
| 9,297,804 B2 | 3/2016 | Palmon et al. | |
| 2002/0173047 A1* | 11/2002 | Hudak | B01L 3/5023 436/178 |
| 2003/0064526 A1 | 4/2003 | Niedbala et al. | |
| 2003/0124332 A1 | 7/2003 | Mao et al. | |
| 2006/0003394 A1 | 1/2006 | Song | |
| 2006/0246600 A1 | 11/2006 | Yang et al. | |
| 2008/0076169 A1 | 3/2008 | Miles et al. | |
| 2008/0118397 A1 | 5/2008 | Slowey et al. | |
| 2009/0117665 A1* | 5/2009 | Tung | B01L 3/5023 436/501 |
| 2009/0123976 A1 | 5/2009 | Birnboim et al. | |
| 2009/0143699 A1 | 6/2009 | Wu et al. | |
| 2010/0092993 A1 | 4/2010 | Hsieh et al. | |
| 2010/0099149 A1 | 4/2010 | Birnboim et al. | |
| 2010/0255512 A1 | 10/2010 | Wu et al. | |
| 2010/0331725 A1 | 12/2010 | Libby et al. | |
| 2012/0310113 A1 | 12/2012 | Giddings et al. | |
| 2015/0198592 A1 | 7/2015 | Wang | |
| 2016/0131645 A1 | 5/2016 | Wang | |
| 2017/0212108 A1 | 7/2017 | Li et al. | |
| 2017/0242045 A1* | 8/2017 | Letourneau | G01N 33/531 |

FOREIGN PATENT DOCUMENTS

| | | |
|---|---|---|
| EP | 1566640 A1 | 8/2005 |
| WO | 03/028889 A1 | 4/2003 |
| WO | 03/104251 A2 | 12/2003 |
| WO | 2007/068094 A1 | 6/2007 |
| WO | 2008/091572 A1 | 7/2008 |
| WO | 2008/131033 A1 | 10/2008 |
| WO | 2010/118067 A1 | 10/2010 |
| WO | 2010/130055 A1 | 11/2010 |
| WO | 2011/116481 A1 | 9/2011 |
| WO | 2013/012785 A1 | 1/2013 |
| WO | 2013/153461 A2 | 10/2013 |
| WO | 2014/120963 A1 | 8/2014 |
| WO | 2014/201307 A1 | 12/2014 |
| WO | 2015/131291 A1 | 9/2015 |
| WO | 2015/172250 A1 | 11/2015 |
| WO | 2016/029020 A1 | 2/2016 |
| WO | 2016/044338 A2 | 3/2016 |
| WO | 2016/164365 A1 | 10/2016 |
| WO | 2016/166415 A1 | 10/2016 |
| WO | 2018/158768 A1 | 9/2018 |
| WO | 2019/159167 A1 | 8/2019 |

OTHER PUBLICATIONS

International Search Report for PCT/IL2019/050171 dated Jul. 25, 2019 (PCT/ISA/210).
Written Opinion for PCT/IL2019/050171 dated Jul. 25, 2019 (PCT/ISA/237).
U.S. Appl. No. 62/630,516, filed Feb. 14, 2018.
Biosynex COVID-19 Ag BSS [package insert]. Fribourg, Switzerland: Biosynex Swiss SA; 2020.
POREX Filtration Group. (May 2019). Sample Data Sheet.
POREX Filtration Group. (2020). Sample order.
Liu, Jie, et al. "Preparation and characterization of carboxymethylcellulose hydrogel fibers." Journal of Engineered Fibers and Fabrics 13.3 (2018): 155892501801300302.
Zymo Research. (2016). DNA/RNA ShieldTM Protocol. https://files.zymoresearch.com/protocols/_r1100-50_r1100-250_r1200-25_r1100-125_dna_rna_shield.pdf.
Zymo Research. (2016b). DNA/RNA ShieldTM Safety Data Sheet. https://files.zymoresearch.com/sds/_r1100-50_r1100-250_r1200-25_r1100-125_dna_rna_shield.pdf.
An Office Action dated Jun. 29, 2021, which issued during the prosecution of European Patent Application No. 19707887.6.
Partial International Search Report dated Oct. 5, 2021, which issued during the prosecution of Applicant's PCT/IL2021/050697.
Pure•SAL™—Oasis Diagnostics®. (Jan. 15, 2018). Oasis Diagnostics. Retrieved Jan. 1, 2022, from https://web.archive.org/web/20180115090553/http://4saliva.com/products/pure-sal/.
Written Opinion of the International Searching Authority dated Jul. 25, 2019 in International Application No. PCT/IL2021/050697.
Updated International Search Report dated Dec. 23, 2021 in International Application No. PCT/IL2021/050697.

* cited by examiner

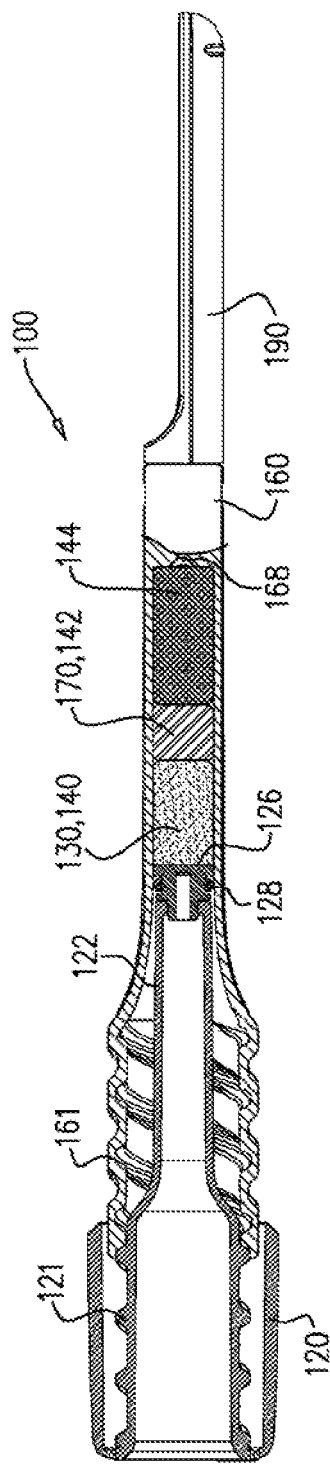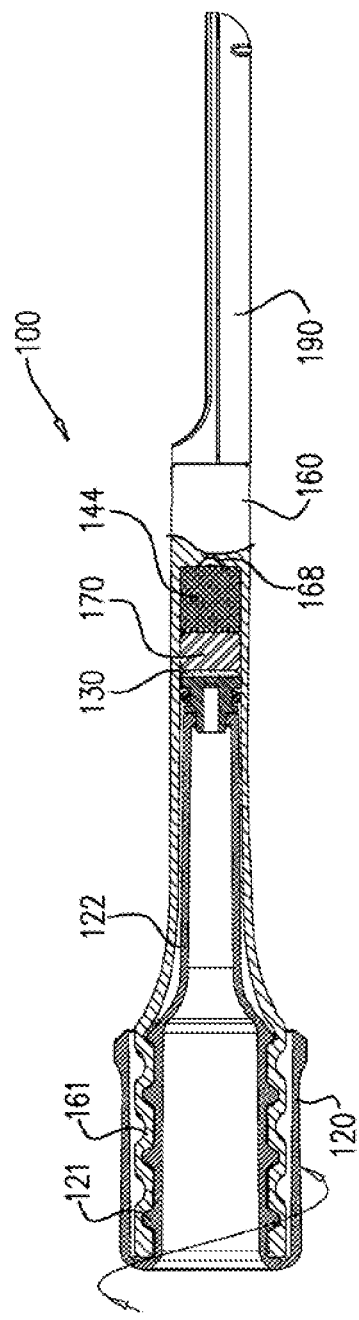
FIG. 4A
FIG. 4B

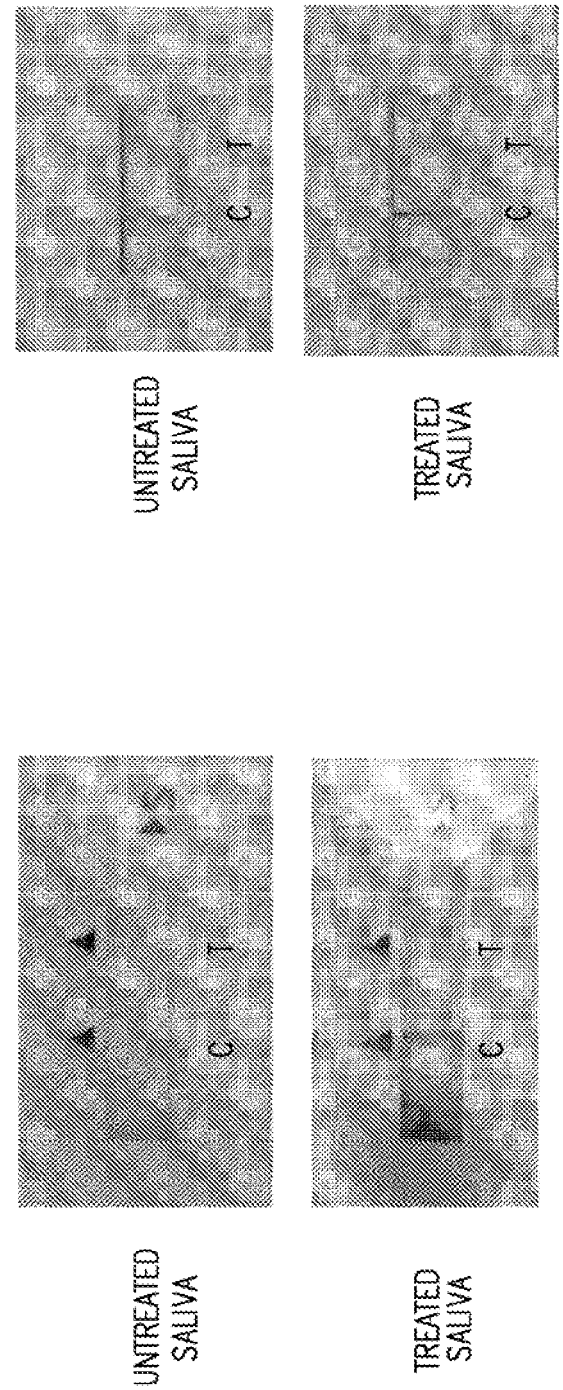

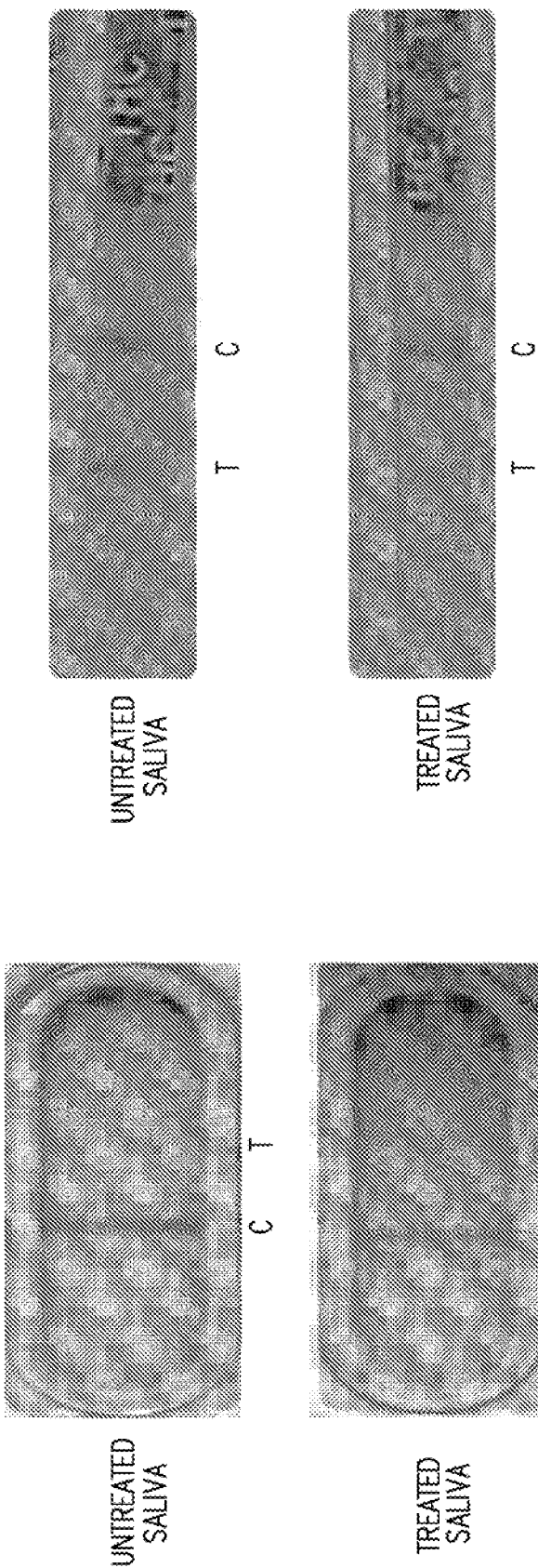

METHODS AND APPARATUS FOR DETECTING ANALYTES

CROSS-REFERENCES TO RELATED APPLICATIONS

This patent application is the US National Phase of International Patent Application PCT/IL2019/050171 to Deutsch et al., entitled "Methods and apparatus for detecting analytes," filed Feb. 13, 2019, which published as WO 2019/159167, and which claims priority from U.S. Provisional Patent Application 62/630,516 to Krief et al., filed Feb. 14, 2018, and entitled "Methods and apparatus for detecting analytes in saliva," which is incorporated herein by reference.

FIELD OF THE INVENTION

Some applications of the present invention generally relate to medical apparatus and methods. Specifically, some applications of the present invention relate to apparatus and methods for detecting analytes in tissue samples such as body fluids.

BACKGROUND

Tests are performed on body fluids to detect the presence and/or concentration of various analytes, in order to determine a condition of the subject. It is important that such tests are sufficiently sensitive and reliable. For some conditions, such tests are performed frequently, and convenience is important. Lateral flow tests are commonly used for detecting analytes in body fluids. For example, lateral flow dipstick tests are commonly used to detect pregnancy by detecting human chorionic gonadotropin in the urine of a subject.

A factor affecting the convenience of a given test is the body fluid that is tested. For example, it is typically more convenient to sample urine than to sample blood. Similarly, it is typically more convenient to sample saliva than to sample urine. However, there may be a trade-off between convenience and sensitivity and reliability. For example, lateral flow dipstick tests somewhat reliably detect human chorionic gonadotropin (HCG) in urine, but even though it would be more convenient to test saliva, current lateral flow tests cannot reliably detect HCG in saliva.

SUMMARY OF THE INVENTION

In accordance with some applications of the present invention, the detectability of an analyte in a body fluid such as saliva is increased by introducing the body fluid into a stationary phase (e.g., passing the body fluid through the stationary phase) prior to analyzing the body fluid. Typically, the body fluid is passed through the stationary phase such that an eluate derived from the body fluid emerges from the stationary phase and passes into a lateral flow platform. Typically, the stationary phase is cellulosic, e.g., comprising cotton and/or carboxymethyl cellulose (e.g., fibers thereof).

For some applications, an eluent is also introduced into the stationary phase. For some such applications, the eluent comprises a protein, such as an albumin. For some applications, the protein is dissolved in the body fluid prior to introduction into the stationary phase. For example, the protein may be initially held within a porous carrier, and the body fluid may be passed through the carrier, dissolving the protein, such that the protein, dissolved in the body fluid, passes into the stationary phase.

For some applications, a polyoxyethylene-polyoxypropylene block copolymer (e.g., poly(ethylene glycol)-block-poly(propylene glycol)-block-poly(ethylene glycol)) is introduced prior to analyzing the body fluid (e.g., prior to the body fluid passing into the lateral flow platform).

For some applications, a system is provided that facilitates simple use of the techniques described herein. For example, the system may comprise (i) the carrier with the protein disposed therein, (ii) the stationary phase, and (iii) the lateral flow platform, the components arranged such that the body fluid (and/or the eluent derived therefrom) passes through the carrier and the stationary phase to the lateral flow platform, e.g., in response to a simple operation (such as a single movement) by the user. For some applications, the system comprises a barrel within which the carrier and the stationary phase are disposed, and a plunger configured to push the fluid therethrough. For some applications, a sponge attached to a distal end of the plunger is used to obtain the body fluid, and to introduce the body fluid into the barrel. For some such applications, subsequent advancement of the plunger within the barrel squeezes the fluid out of the sponge, through the carrier, through the stationary phase, and into the lateral flow platform.

Typically, the analyte (if present) is detected in order to determine a condition of the subject. For example, a presence and/or a concentration of human chorionic gonadotropin (HCG) within the eluent may be detected, and it may be determined that the subject is pregnant, or not pregnant, based upon the presence and/or concentration of human chorionic gonadotropin.

There is therefore provided, in accordance with an application of the present invention, a method, including: introducing a body fluid of a subject into a channel within which a cellulosic stationary phase is disposed; and passing the fluid through the stationary phase such that an eluate derived from the fluid emerges from the stationary phase and passes into a lateral flow platform.

In an application, the stationary phase includes cellulosic fibers, and introducing the fluid includes introducing the fluid into the channel within which the stationary phase that includes the cellulosic fibers is disposed.

In an application, the stationary phase includes cotton, and introducing the fluid includes introducing the fluid into the channel within which the stationary phase that includes cotton is disposed.

In an application, the stationary phase includes carboxymethyl cellulose (CMC), and introducing the fluid includes introducing the fluid into the channel within which the stationary phase that includes CMC is disposed.

In an application, the method further includes obtaining the fluid by inserting a sponge into the subject such that the fluid is absorbed into the sponge.

In an application, the fluid is saliva, and introducing the fluid includes introducing the saliva.

In an application, the fluid is urine, and introducing the fluid includes introducing the urine.

In an application, the method further includes analyzing the eluate for an analyte using the lateral flow platform.

In an application, the analyte is human chorionic gonadotropin (HCG), and analyzing the eluate for the analyte includes analyzing the eluate for HCG.

In an application, the analyte is histidine-rich protein 2 (HRPII), and analyzing the eluate for the analyte includes analyzing the eluate for HRPII.

In an application, the analyte is pan-*Plasmodium* antigen lactate dehydrogenase (pLDH), and analyzing the eluate for the analyte includes analyzing the eluate for pLDH.

In an application, the analyte is luteinizing hormone (LH), and analyzing the eluate for the analyte includes analyzing the eluate for LH.

In an application, the analyte is a *Helicobacter pylori* antigen, and analyzing the eluate for the analyte includes analyzing the eluate for the *Helicobacter pylori* antigen.

In an application, the analyte is a *Candida* spp. antigen, and analyzing the eluate for the analyte includes analyzing the eluate for the *Candida* spp. antigen.

In an application, the analyte is tetrahydrocannabinol (THC), and analyzing the eluate for the analyte includes analyzing the eluate for THC.

In an application, the method further includes introducing a protein into the stationary phase.

In an application, the protein is an albumin, and introducing the protein into the stationary phase includes introducing the albumin into the stationary phase.

In an application, the method further includes dissolving the albumin in the fluid, and introducing the albumin into the stationary phase includes introducing, into the stationary phase, the albumin dissolved in the fluid.

In an application, dissolving the albumin in the fluid includes passing the fluid through a porous carrier within which the albumin is disposed.

In an application:

a polyoxyethylene-polyoxypropylene block copolymer is disposed within the carrier, and passing the fluid through the carrier includes passing the fluid through the carrier such that the polyoxyethylene-polyoxypropylene block copolymer dissolves in the fluid.

In an application, the polyoxyethylene-polyoxypropylene block copolymer is poly(ethylene glycol)-block-poly(propylene glycol)-block-poly(ethylene glycol), and passing the fluid through the carrier such that the polyoxyethylene-polyoxypropylene block copolymer dissolves in the fluid includes passing the fluid through the carrier such that the poly(ethylene glycol)-block-poly(propylene glycol)-block-poly(ethylene glycol) dissolves in the fluid.

In an application, the carrier and the stationary phase are disposed in series within a channel, and dissolving the albumin in the fluid and introducing the albumin into the stationary phase, include dissolving the albumin in the fluid and introducing the albumin into the stationary phase by moving the fluid along the channel through the carrier and into the stationary phase.

In an application, moving the fluid along the channel through the carrier and into the stationary phase includes moving the fluid along the channel through the carrier and into the stationary phase by advancing a plunger through a first portion of the channel.

In an application, extracting the eluate from the stationary phase includes advancing the plunger further, through a second portion of the channel.

In an application, advancing the plunger through the second portion of the channel includes advancing the plunger through the second portion of the channel such that the eluate moves from the stationary phase to a lateral flow platform.

In an application, extracting the eluate from the stationary phase includes compressing the stationary phase by advancing the plunger through the second portion of the channel.

In an application, introducing the fluid into the channel includes introducing the fluid into the channel while the fluid is disposed within a sponge coupled to the plunger.

In an application, moving the fluid along the channel through the carrier and into the stationary phase includes using the plunger to compress the sponge within the channel.

In an application, using the plunger to compress the sponge within the channel includes using the sponge to compress the sponge between the plunger and the carrier.

In an application, moving the fluid along the channel through the carrier and into the stationary phase includes using the plunger to compress the carrier between the sponge and the stationary phase.

In an application, introducing the protein into the stationary phase includes introducing an eluent containing the protein into the stationary phase, subsequently to introducing the fluid into the channel.

There is further provided, in accordance with an application of the present invention, a method, including:

introducing a body fluid of a subject into a cellulosic stationary phase, the fluid including an analyte;

introducing a protein into the stationary phase; and extracting an eluate from the stationary phase, the eluate including the analyte.

In an application, the stationary phase includes cellulosic fibers, and introducing the fluid includes introducing the fluid into the stationary phase that includes the cellulosic fibers.

In an application, the stationary phase includes cotton, and introducing the fluid includes introducing the fluid into the stationary phase that includes cotton.

In an application, the stationary phase includes carboxymethyl cellulose (CMC), and introducing the fluid includes introducing the fluid into the stationary phase that includes CMC.

In an application, the fluid is urine, and introducing the fluid includes introducing the urine.

In an application, the protein is an albumin, and introducing the protein into the stationary phase includes introducing the albumin into the stationary phase.

In an application, the albumin is a serum albumin, and introducing the albumin into the stationary phase includes introducing the serum albumin into the stationary phase.

In an application, the serum albumin is a mammalian serum albumin, and introducing the serum albumin into the stationary phase includes introducing the mammalian serum albumin into the stationary phase.

In an application, the mammalian serum albumin is bovine serum albumin, and introducing the mammalian serum albumin into the stationary phase includes introducing the bovine serum albumin into the stationary phase.

In an application, the mammalian serum albumin is human serum albumin, and introducing the mammalian serum albumin into the stationary phase includes introducing the bovine serum albumin into the stationary phase.

In an application, the method further includes analyzing the eluate for the analyte.

In an application, the analyte is human chorionic gonadotropin (HCG), and analyzing the eluate for the analyte includes analyzing the eluate for HCG.

In an application, the analyte is histidine-rich protein 2 (HRPII), and analyzing the eluate for the analyte includes analyzing the eluate for HRPII.

In an application, the analyte is pan-*Plasmodium* antigen lactate dehydrogenase (pLDH), and analyzing the eluate for the analyte includes analyzing the eluate for pLDH.

In an application, the analyte is luteinizing hormone (LH), and analyzing the eluate for the analyte includes analyzing the eluate for LH.

In an application, the analyte is a *Helicobacter pylori* antigen, and analyzing the eluate for the analyte includes analyzing the eluate for the *Helicobacter pylori* antigen.

In an application, the analyte is a *Candida* spp. antigen, and analyzing the eluate for the analyte includes analyzing the eluate for the *Candida* spp. antigen.

In an application, the analyte is tetrahydrocannabinol (THC), and analyzing the eluate for the analyte includes analyzing the eluate for THC.

In an application, analyzing the eluate for the analyte includes applying the eluate to a lateral flow platform.

In an application, analyzing the eluate for the analyte includes performing an immunoassay on the analyte.

In an application, the method further includes dissolving the protein in the fluid, and introducing the protein into the stationary phase includes introducing, into the stationary phase, the protein dissolved in the fluid.

In an application, dissolving the protein in the fluid includes passing the fluid through a porous carrier within which the protein is disposed.

In an application:

a polyoxyethylene-polyoxypropylene block copolymer is disposed within the carrier, and passing the fluid through the carrier includes passing the fluid through the carrier such that the polyoxyethylene-polyoxypropylene block copolymer dissolves in the fluid.

In an application, the polyoxyethylene-polyoxypropylene block copolymer is poly(ethylene glycol)-block-poly(propylene glycol)-block-poly(ethylene glycol), and passing the fluid through the carrier such that the polyoxyethylene-polyoxypropylene block copolymer dissolves in the fluid includes passing the fluid through the carrier such that the poly(ethylene glycol)-block-poly(propylene glycol)-block-poly(ethylene glycol) dissolves in the fluid.

In an application, the carrier and the stationary phase are disposed in series within a channel, and dissolving the protein in the fluid and introducing the protein into the stationary phase, include dissolving the protein in the fluid and introducing the protein into the stationary phase by moving the fluid along the channel through the carrier and into the stationary phase.

In an application, moving the fluid along the channel through the carrier and into the stationary phase includes moving the fluid along the channel through the carrier and into the stationary phase by advancing a plunger through a first portion of the channel.

In an application, extracting the eluate from the stationary phase includes advancing the plunger further, through a second portion of the channel.

In an application, advancing the plunger through the second portion of the channel includes advancing the plunger through the second portion of the channel such that the eluate moves from the stationary phase to a lateral flow platform.

In an application, extracting the eluate from the stationary phase includes compressing the stationary phase by advancing the plunger through the second portion of the channel.

In an application, the method further includes introducing a sponge into the channel, the sponge coupled to the plunger, and the fluid disposed within the sponge.

In an application, moving the fluid along the channel through the carrier and into the stationary phase includes using the plunger to compress the sponge within the channel.

In an application, using the plunger to compress the sponge within the channel includes using the sponge to compress the sponge between the plunger and the carrier.

In an application, moving the fluid along the channel through the carrier and into the stationary phase includes using the plunger to compress the carrier between the sponge and the stationary phase.

In an application, the fluid is saliva, and introducing the fluid includes introducing the saliva.

In an application, the method further includes obtaining the saliva by placing a sponge into a mouth of the subject such that the saliva is absorbed into the sponge.

In an application, introducing the protein into the stationary phase includes introducing an eluent containing the protein into the stationary phase, subsequently to introducing the fluid into the stationary phase.

There is further provided, in accordance with an application of the present invention, apparatus, including:

an elongate barrel, shaped to define a channel therethrough, the barrel having:

an opening into the channel at a proximal region of the barrel, and an outlet from the channel at a distal region of the barrel;

a cellulosic stationary phase, disposed within the channel between the carrier and the distal region of the barrel;

a lateral flow platform, coupled to the distal region of the barrel such that a sample pad of the lateral flow platform is in fluid communication with the outlet; and a plunger, having a distal portion that is introducible into the channel via the opening, and is dimensioned to slide snugly within the channel.

In an application, the stationary phase includes cellulosic fibers.

In an application, the stationary phase includes cotton.

In an application, the stationary phase includes carboxymethyl cellulose (CMC).

In an application, the lateral flow platform includes a human chorionic gonadotropin (HCG) lateral flow test including antibodies specific to HCG.

In an application, the lateral flow platform includes a *Plasmodium* flow test including antibodies specific to histidine-rich protein 2 (HRPII).

In an application, the lateral flow platform includes a *Plasmodium* flow test including antibodies specific to pan-*Plasmodium* antigen lactate dehydrogenase (pLDH).

In an application, the lateral flow platform includes a luteinizing hormone (LH) flow test including antibodies specific to LH.

In an application, the lateral flow platform includes a *Helicobacter pylori* flow test including antibodies specific to a *Helicobacter pylori* antigen.

In an application, the lateral flow platform includes a *Candida* flow test including antibodies specific to a *Candida* spp. antigen.

In an application, the lateral flow platform includes a tetrahydrocannabinol (THC) flow test including antibodies specific to THC.

In an application, the apparatus further includes:

a porous carrier, disposed within the channel; and a protein, held in the carrier.

In an application, the protein is an albumin.

In an application, the albumin is bovine serum albumin.

In an application, the protein is dried.

In an application, the apparatus further includes a polyoxyethylene-polyoxypropylene block copolymer, positioned fluidically between the carrier and the lateral flow platform, inclusive.

In an application, the polyoxyethylene-polyoxypropylene block copolymer is held in the carrier.

In an application, the polyoxyethylene-polyoxypropylene block copolymer is held in the lateral flow platform.

In an application, the polyoxyethylene-polyoxypropylene block copolymer is held in the stationary phase.

In an application, the polyoxyethylene-polyoxypropylene block copolymer is poly(ethylene glycol)-block-poly(propylene glycol)-block-poly(ethylene glycol).

In an application, the apparatus further includes a sponge coupled to the distal portion of the plunger, and:
the sponge is configured to hold a fluid, and to introduce the sponge holding the fluid into the channel via the opening, and
the plunger is dimensioned such that sliding of the distal portion through the channel compresses the sponge within the channel.

In an application, the apparatus is configured such that, while the sponge holds the fluid, compression of the sponge within the channel drives the fluid:
out of the sponge,
through the carrier, dissolving at least some of the albumin,
with the dissolved albumin, into the stationary phase, and
as an eluate, out of the stationary phase, through the outlet, and onto the sample pad.

In an application, the carrier is sufficiently compressible, and the plunger is dimensioned, such that sliding of the distal portion of the plunger through the channel compresses the carrier between the sponge and the stationary phase.

In an application, the plunger is dimensioned such that the sliding of the distal portion through the channel compresses the sponge between the plunger and the carrier.

In an application, the plunger:
has a proximal portion that includes a screw thread, configured to couple the plunger to the barrel;
includes a stem that extends between the screw thread and the distal portion; and
is dimensioned such that coupling the plunger to the barrel using the screw thread compresses the sponge within the channel by sliding the distal portion through the channel.

In an application, the plunger is dimensioned such that coupling the plunger to the barrel using the screw thread compresses the carrier between the sponge and the stationary phase by sliding the distal portion through the channel.

There is further provided, in accordance with an application of the present invention, apparatus, including:
an elongate barrel, shaped to define a channel therethrough, the barrel having:
an opening into the channel at a proximal region of the barrel, and
an outlet from the channel at a distal region of the barrel;
a porous carrier, disposed within the channel;
an albumin, held in the carrier;
a cellulosic stationary phase, disposed within the channel between the carrier and the distal region of the barrel; and
a plunger, having a distal portion that is introducible into the channel via the opening, and is dimensioned to slide snugly within the channel.

There is further provided, in accordance with an application of the present invention, a method, including:
obtaining saliva of a woman who wishes to know whether she is pregnant; and
subsequently, introducing the saliva into a channel within which a cellulosic stationary phase is disposed.

There is further provided, in accordance with an application of the present invention, a method for performing elution of an analyte from saliva, the method including:
causing the analyte to become adsorbed to a cellulosic stationary-phase adsorbent, by absorbing the saliva within the stationary-phase adsorbent; and
eluting the analyte from the stationary-phase adsorbent, by passing an eluent through the stationary-phase adsorbent.

In an application, the stationary-phase adsorbent includes cellulosic fibers, and causing the analyte to become adsorbed includes causing the analyte to become adsorbed to the stationary-phase adsorbent that includes cellulosic fibers.

In an application, the stationary-phase adsorbent includes cotton, and causing the analyte to become adsorbed includes causing the analyte to become adsorbed to the stationary-phase adsorbent that includes cotton.

In an application, the stationary-phase adsorbent includes carboxymethyl cellulose (CMC), and causing the analyte to become adsorbed includes causing the analyte to become adsorbed to the stationary-phase adsorbent that includes CMC.

In an application, the method further includes extracting a portion of the absorbed saliva from the stationary-phase adsorbent, by applying pressure to the stationary-phase adsorbent.

In an application, the analyte includes human chorionic gonadotropin, and causing the analyte to become adsorbed to the stationary-phase adsorbent includes causing the human chorionic gonadotropin to become adsorbed to a stationary-phase adsorbent.

In an application, the analyte includes an analyte selected from the group consisting of: histidine-rich protein 2 and pan-*Plasmodium* antigen lactate dehydrogenase, and causing the analyte to become adsorbed to the stationary-phase adsorbent includes causing the selected analyte to become adsorbed to a stationary-phase adsorbent.

In an application, the analyte includes luteinizing hormone, and causing the analyte to become adsorbed to the stationary-phase adsorbent includes causing the luteinizing hormone to become adsorbed to a stationary-phase adsorbent.

In an application, the analyte includes a *Helicobacter pylori* antigen, and causing the analyte to become adsorbed to the stationary-phase adsorbent includes causing the *Helicobacter pylori* antigen to become adsorbed to a stationary-phase adsorbent.

In an application, the analyte includes a *Candida* spp. antigen, and causing the analyte to become adsorbed to the stationary-phase adsorbent includes causing the *Candida* spp. antigen to become adsorbed to a stationary-phase adsorbent.

In an application, the analyte includes tetrahydrocannabinol, and causing the analyte to become adsorbed to the stationary-phase adsorbent includes causing the tetrahydrocannabinol to become adsorbed to a stationary-phase adsorbent.

In an application, the method further includes detecting the analyte in the eluent, and determining a condition of the subject in response thereto.

There is further provided, in accordance with an application of the present invention, apparatus for performing elution of an analyte from saliva, the apparatus including:
a cellulosic stationary-phase adsorbent, the stationary-phase adsorbent being configured to adsorb the analyte by absorbing the saliva; and
an eluent configured to elute the analyte from the stationary-phase adsorbent by passing through the stationary-phase adsorbent.

In an application, the stationary-phase adsorbent includes cellulosic fibers.

In an application, the stationary-phase adsorbent includes cotton.

In an application, the stationary-phase adsorbent includes carboxymethyl cellulose (CMC).

In an application, the apparatus further includes a pressure-applying mechanism that is configured to extract a portion of the absorbed saliva from the stationary-phase adsorbent, by applying pressure to the stationary-phase adsorbent.

In an application, the analyte includes human chorionic gonadotropin, and the stationary-phase adsorbent is configured to adsorb the human chorionic gonadotropin.

In an application, the analyte includes an analyte selected from the group consisting of: histidine-rich protein 2 and pan-*Plasmodium* antigen lactate dehydrogenase, and the stationary-phase adsorbent is configured to adsorb the selected analyte.

In an application, the analyte includes luteinizing hormone, and the stationary-phase adsorbent is configured to adsorb the luteinizing hormone.

In an application, the analyte includes a *Helicobacter pylori* antigen, and the stationary-phase adsorbent is configured to adsorb the *Helicobacter pylori* antigen.

In an application, the analyte includes a *Candida* spp. antigen, and the stationary-phase adsorbent is configured to adsorb the *Candida* spp. antigen.

In an application, the analyte includes tetrahydrocannabinol, and the stationary-phase adsorbent is configured to adsorb the tetrahydrocannabinol.

There is further provided, in accordance with an application of the present invention, a method for performing elution of an analyte from saliva, the method including:

causing the analyte to become adsorbed to a stationary-phase adsorbent, by absorbing the saliva within the stationary-phase adsorbent;

extracting a portion of the absorbed saliva from the stationary-phase adsorbent, by applying pressure to the stationary-phase adsorbent; and eluting the analyte from the stationary-phase adsorbent, by passing an eluent through the stationary-phase adsorbent.

In an application, the stationary-phase adsorbent includes cellulosic fibers, and causing the analyte to become adsorbed includes causing the analyte to become adsorbed to the stationary-phase adsorbent that includes cellulosic fibers.

In an application, the stationary-phase adsorbent includes cotton, and causing the analyte to become adsorbed includes causing the analyte to become adsorbed to the stationary-phase adsorbent that includes cotton.

In an application, the stationary-phase adsorbent includes carboxymethyl cellulose (CMC), and causing the analyte to become adsorbed includes causing the analyte to become adsorbed to the stationary-phase adsorbent that includes CMC.

In an application, the analyte includes human chorionic gonadotropin, and causing the analyte to become adsorbed to the stationary-phase adsorbent includes causing the human chorionic gonadotropin to become adsorbed to a stationary-phase adsorbent.

In an application, the analyte includes an analyte selected from the group consisting of: histidine-rich protein 2 and pan-*Plasmodium* antigen lactate dehydrogenase, and causing the analyte to become adsorbed to the stationary-phase adsorbent includes causing the selected analyte to become adsorbed to a stationary-phase adsorbent.

In an application, the analyte includes luteinizing hormone, and causing the analyte to become adsorbed to the stationary-phase adsorbent includes causing the luteinizing hormone to become adsorbed to a stationary-phase adsorbent.

In an application, the analyte includes a *Helicobacter pylori* antigen, and causing the analyte to become adsorbed to the stationary-phase adsorbent includes causing the *Helicobacter pylori* antigen to become adsorbed to a stationary-phase adsorbent.

In an application, the analyte includes a *Candida* spp. antigen, and causing the analyte to become adsorbed to the stationary-phase adsorbent includes causing the *Candida* spp. antigen to become adsorbed to a stationary-phase adsorbent.

In an application, the analyte includes tetrahydrocannabinol, and causing the analyte to become adsorbed to the stationary-phase adsorbent includes causing the tetrahydrocannabinol to become adsorbed to a stationary-phase adsorbent.

In an application, the method further includes detecting the analyte in the eluent, and determining a condition of the subject in response thereto.

In an application, causing the analyte to become adsorbed to the stationary-phase adsorbent includes causing the analyte to become adsorbed to a stationary-phase adsorbent that includes cotton and carboxymethyl cellulose.

There is further provided, in accordance with an application of the present invention, apparatus for performing elution of an analyte from saliva, the apparatus including:

a stationary-phase adsorbent configured to adsorb the analyte by absorbing the saliva;

a pressure-applying mechanism that is configured to extract a portion of the absorbed saliva from the stationary-phase adsorbent, by applying pressure to the stationary-phase adsorbent; and an eluent configured to elute the analyte from the stationary-phase adsorbent by passing through the stationary-phase adsorbent.

In an application, the stationary-phase adsorbent includes cellulosic fibers.

In an application, the stationary-phase adsorbent includes cotton.

In an application, the stationary-phase adsorbent includes carboxymethyl cellulose (CMC).

In an application, the analyte includes human chorionic gonadotropin, and the stationary-phase adsorbent is configured to adsorb the human chorionic gonadotropin.

In an application, the analyte includes an analyte selected from the group consisting of: histidine-rich protein 2 and pan-*Plasmodium* antigen lactate dehydrogenase, and the stationary-phase adsorbent is configured to adsorb the selected analyte.

In an application, the analyte includes luteinizing hormone, and the stationary-phase adsorbent is configured to adsorb the luteinizing hormone.

In an application, the analyte includes a *Helicobacter pylori* antigen, and the stationary-phase adsorbent is configured to adsorb the *Helicobacter pylori* antigen.

In an application, the analyte includes a *Candida* spp. antigen, and the stationary-phase adsorbent is configured to adsorb the *Candida* spp. antigen.

In an application, the analyte includes tetrahydrocannabinol, and the stationary-phase adsorbent is configured to adsorb the tetrahydrocannabinol.

In an application, the stationary-phase adsorbent includes cotton and carboxymethyl cellulose.

There is further provided, in accordance with an application of the present invention, a method for detecting an analyte in saliva of a subject, including:

collecting the saliva in a receptacle;

passing the collected saliva through a stationary phase-adsorbent that includes cotton and carboxymethyl cellulose;

detecting an analyte that was within the saliva after the analyte has passed through the stationary-phase adsorbent; and determining a condition of the subject, in response thereto.

In an application, the stationary-phase adsorbent includes cellulosic fibers, and passing the collected saliva through the stationary phase-adsorbent includes passing the collected saliva through the stationary phase-adsorbent that includes cellulosic fibers.

In an application, the stationary-phase adsorbent includes cotton, and passing the collected saliva through the stationary phase-adsorbent includes passing the collected saliva through the stationary phase-adsorbent that includes cotton.

In an application, the stationary-phase adsorbent includes carboxymethyl cellulose (CMC), and passing the collected saliva through the stationary phase-adsorbent includes passing the collected saliva through the stationary phase-adsorbent that includes CMC.

In an application, passing the collected saliva through the stationary phase-adsorbent includes passing the collected saliva through the stationary phase-adsorbent, one or more agents being disposed upon the stationary phase adsorbent.

In an application, passing the collected saliva through the stationary phase-adsorbent includes causing a medium, within which the analytes are disposed, to change, in a manner that increases the detectability of the analytes.

In an application, detecting the analyte includes detecting human chorionic gonadotropin.

In an application, detecting the analyte includes detecting an analyte selected from the group consisting of: histidine-rich protein 2 and pan-*Plasmodium* antigen lactate dehydrogenase.

In an application, detecting the analyte includes detecting luteinizing hormone.

In an application, detecting the analyte includes detecting a *Helicobacter pylori* antigen.

In an application, detecting the analyte includes detecting a *Candida* spp. antigen.

In an application, detecting the analyte includes detecting tetrahydrocannabinol.

The present invention will be more fully understood from the following detailed description of embodiments thereof, taken together with the drawings, in which:

BRIEF DESCRIPTION OF THE DRAWINGS

FIGS. 3 and 4A-B are schematic illustrations of a system for use with a body fluid of a subject, in accordance with some applications of the invention; and FIGS. 5, 6, 7, 8, 9, 10, 11, 12, 13, and 14 show results of various lateral flow test assays, performed on untreated body fluids, or on body fluids treated according to an application of the invention.

DETAILED DESCRIPTION OF EMBODIMENTS

Figure 1:
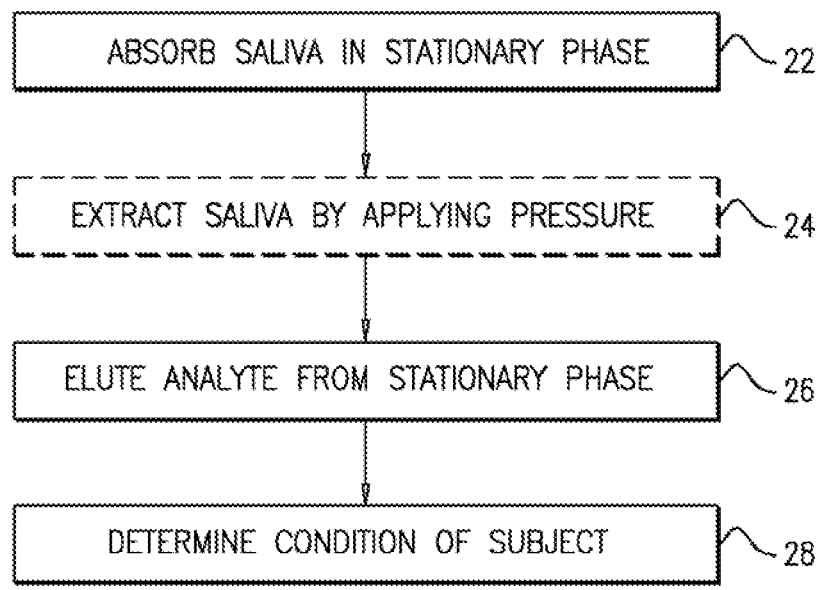
FIG. 1 is a schematic illustration of a method that is performed, in accordance with some applications of the present invention.

Reference is now made to FIG. 1, which is a flowchart showing at least some steps of a method that is performed, in accordance with some applications of the present invention.

Typically, in a first step 22 saliva or another body fluid from a subject is introduced into (e.g., absorbed within) a stationary phase (e.g., a stationary-phase adsorbent). The stationary phase may be configured to adsorb an analyte from the saliva, if the analyte is present. Typically, the stationary phase is cellulosic. For example, the stationary phase may include cotton, carboxymethyl cellulose (CMC), or both. For some applications, a ratio of cotton to CMC within the stationary phase is between 5:1 and 50:1 (e.g., between 10:1 and 25:1).

For some applications, in a second step 24, a portion of the absorbed saliva (i.e., an eluate) is extracted from the stationary phase, by applying pressure to the stationary phase. For example, and as described in more detail hereinbelow, a dedicated pressure-applying mechanism may be used for extracting the portion of the absorbed saliva from the stationary phase. For example, two or more pressure-applying surfaces may be configured to squeeze the stationary phase therebetween, in response to a subject pushing and/or otherwise applying pressure to one of the pressure-applying surfaces. It is noted that step 24 is optional (as indicated by the dashed box around step 24), and for some applications, the method proceeds to step 26, without step 24 being performed prior to step 26.

In a third step 26, the analyte (if any is present) is eluted from the stationary phase, by passing an eluent through the stationary phase, the resulting eluate containing the analyte. For some applications, the eluent contains a protein, such as an albumin, such as a serum albumin (e.g., a mammalian serum albumin, such as bovine serum albumin (BSA) or human serum albumin (HSA)) or an egg albumin (e.g., ovalbumin).

For some applications, steps 22, 24, and/or 26 are performed simultaneously with each other. For example, the saliva and the eluent may be passed through the stationary phase simultaneously with each other. Alternatively or additionally, pressure may be applied to the stationary phase at the same time as passing the eluent through the stationary phase adsorbent. For some applications, agents are predisposed upon the stationary phase-adsorbent or upon another element (e.g., in dried or powdered form), as described in further detail hereinbelow. Typically, passing through the stationary phase adsorbent (and/or passing through the stationary phase and then being eluted from the stationary phase, and/or passing through the stationary phase that has the agents disposed thereon), causes the medium within which the analytes are disposed to change, in a manner that increases the detectability of the analytes.

In a fourth step 28, the analyte (if any is present), having passed through the stationary phase is detected, e.g., in order to determine a condition of the subject. For some applications, the presence and/or concentration of the analyte is detected using an immunochemical test, such as a lateral flow test, e.g., such as is used in urine dipstick tests, *mutatis mutandis*. Alternatively or additionally, other techniques are used to detect the presence and/or concentration of the analyte. For example, spectrophotometry, mass spectrophotometry, chromatography, or other chemical or physical tests may be used.

Figure 2:
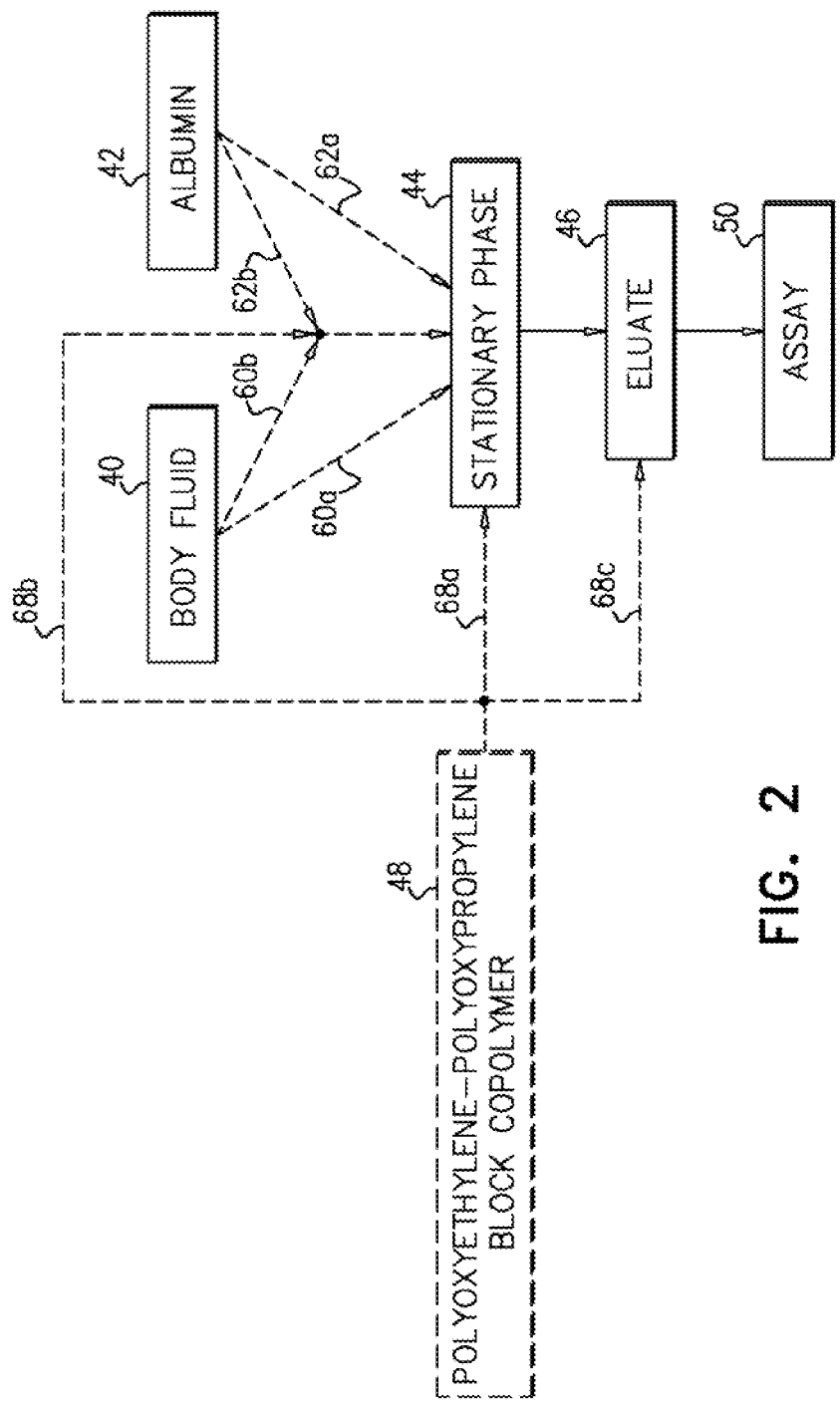
FIG. 2 is a schematic illustration of a method that is performed, in accordance with some applications of the present invention.

Reference is now made to FIG. 2, which is a schematic illustration of a method that is performed, in accordance with some applications of the present invention. For some applications, FIG. 2 is an alternative representation of the technique described with reference to FIG. 1.

A body fluid (e.g., saliva, urine, blood) 40 of a subject is introduced into a stationary phase 44. Stationary phase 44 is typically cellulosic. For example, stationary phase 44 may comprise cotton, CMC, or both. A protein, such as an albumin 42, is also introduced into stationary phase 44. It is to be noted that although the present application typically refers to albumin 42, for some applications a different protein may be used.

For some applications, fluid 40 and albumin 42 are introduced separately into stationary phase 44. This is represented by arrows 60a and 62a, respectively. For some such applications, fluid 40 is introduced first, and the albumin is introduced subsequently, e.g., as a component of an eluent, e.g., as described hereinabove. Alternatively, albumin 42 may be introduced first, and fluid 40 is introduced subsequently.

For some applications, fluid 40 and albumin 42 are introduced simultaneously (e.g., together) into stationary phase 44. This is represented by converging arrows 60b and 62b. For some such applications, albumin 42 is mixed and dissolved into fluid 40, and the mixture/solution is introduced into stationary phase 44. An example of such an application is described with reference to FIGS. 3 and 4A-B.

An eluate 46 is extracted from stationary phase 44. If fluid 40 contained the analyte of interest, eluate 46 contains the analyte. An assay 50 is performed on eluate 46, in order to determine a property of the analyte within the eluate—e.g., the presence and/or concentration of the analyte within the eluate.

It is hypothesized by the inventors that the method described herein, in which fluid 40 is exposed to stationary phase 44 in the presence of albumin 42, increases the sensitivity, specificity, and/or reproducibility of assay 50, compared to performing the assay on fluid 40 without performing this method.

For some applications, a surfactant, typically a polyoxyethylene-polyoxypropylene block copolymer 48, is introduced prior to analysis 50. For some such applications, copolymer 48 is introduced into to stationary phase 44. For example, copolymer 48 may be introduced separately from fluid 40 and albumin 42 (represented by arrow 68a), or simultaneously/together with the fluid and the albumin (represented by arrow 68b), such as by being mixed and/or dissolved into fluid 40. Alternatively or additionally, copolymer 48 may be introduced subsequently to the extraction of eluate 46 from stationary phase 44 (represented by arrow 68c), such as by mixing and/or dissolving the copolymer into eluate 46. For some applications, copolymer 48 is poly(ethylene glycol)-block-poly(propylene glycol)-block-poly(ethylene glycol) (e.g., Synperonic(R) F 108).

It is hypothesized by the inventors that such use of copolymer 48 further increases the sensitivity, specificity, and/or reproducibility of assay 50, e.g., for applications in which assay 50 is a lateral flow test. For example, copolymer 48 may improve flow through the lateral flow strip.

For some applications, the analyte comprises human chorionic gonadotropin (HGC). For example, the presence and/or concentration of HCG may be detected, and it is determined that the subject is pregnant or not pregnant, based upon the detected presence and/or concentration of HCG. Alternatively or additionally, a stage of a subject's pregnancy may be determined based upon the determined presence and/or concentration of HCG.

For some applications, the analyte comprises luteinizing hormone (LH). For example, the presence and/or concentration of LH may be detected, and based upon the detected presence and/or concentration of LH, a stage in the menstrual cycle of the subject may be determined—e.g., it may be determined whether the subject is currently ovulating.

For some applications, the analyte comprises histidine-rich protein (HRP) II and/or pan-*Plasmodium* antigen lactate dehydrogenase. For example, the presence and/or concentration of histidine-rich protein 2 and/or pan-*Plasmodium* antigen lactate dehydrogenase is detected, and it is determined that the subject is suffering from malaria, or is not suffering from malaria, based upon the detected presence and/or concentration of histidine-rich protein 2 and/or pan-*Plasmodium* antigen lactate dehydrogenase.

For some applications, the analyte comprises a *Helicobacter pylori* (*H. pylori*) antigen, such as CagA. For example, the presence and/or concentration of the *H. pylori* antigen is detected, and it is determined that the subject carries *H. pylori*, or does not carry *H. pylori*, based upon the detected presence and/or concentration of the *H. pylori* antigen.

For some applications, the analyte comprises a *Candida* spp. (e.g. *C. albicans*) antigen, such as *Candida albicans* enolase. For example, the presence and/or concentration of the *Candida* antigen is detected, and it is determined that the subject carries *Candida*, or does not carry *Candida*, based upon the detected presence and/or concentration of the *Candida* antigen.

For some applications, the analyte comprises a medical or recreational drug, a component thereof, and/or a metabolite thereof. For example, the presence and/or concentration of tetrahydrocannabinol (THC) is detected, and it is determined that the subject has consumed cannabis or a cannabis product, based upon the detected presence and/or concentration of THC. Alternatively or additionally, a concentration of the drug, drug component, or component thereof within the subject (e.g., within the blood of the subject) may be determined based upon the detected presence and/or concentration of the drug, drug component, or component thereof. Alternatively or additionally, the time since consumption of the drug may be determined based upon the detected presence and/or concentration of the drug, drug component, or component thereof. For applications in which the drug is a medical drug, dosing of the medical drug may also be controlled and/or adjusted based on the detected presence and/or concentration of the drug, drug component, or component thereof.

As described hereinabove, for some applications, a cellulosic stationary phase is used in conjunction with the techniques described herein. In experiments performed by the inventors of the present application, the concentration of HCG in saliva samples was measured. Subsequently, the saliva samples were absorbed into a stationary phase that included cotton and carboxymethyl cellulose at a cotton:CMC ratio of between 10:1 and 25:1, and the saliva portions were then squeezed out of the adsorbent. It was found that the concentration of HCG in the saliva samples after the samples had been absorbed and then extracted from the stationary phase was substantially reduced relative the original concentrations in the respective samples. These results indicate that a cellulosic stationary phase (e.g., comprising cotton and/or CMC) is effective at adsorbing at least some analytes from saliva. Therefore, in accordance with some applications of the present invention, a cellulosic stationary phase is used.

For some applications, saliva from the subject is collected in a receptacle. Subsequently, the saliva is passed through a cellulosic stationary phase-adsorbent. For some applications, the stationary phase comprises cotton and CMC, e.g., at a cotton:CMC ratio of between 5:1 and 50:1 (e.g., between 10:1 and 25:1). For some applications, agents are disposed upon the stationary phase adsorbent (e.g., in dried and/or powdered form). Typically, passing through the stationary phase adsorbent (and/or passing through the stationary phase, which has the agents disposed thereon), causes the medium within which the analytes are disposed to change, in a manner that increases the detectability of the analytes. Typically, the analyte (if any is present), having passed through the stationary phase is detected in order to determine a condition of the subject, e.g., in accordance with the techniques described hereinabove. It is noted that the technique described in this paragraph differs from techniques in which a stationary phase is used for the purpose of collecting a subject's saliva, such that the saliva may then be analyzed. Rather, in accordance with the technique described herein, saliva that has already been collected is made to pass through the stationary phase, typically, for the purpose of increasing the detectability of analytes that are present within the saliva.

Figure 3:
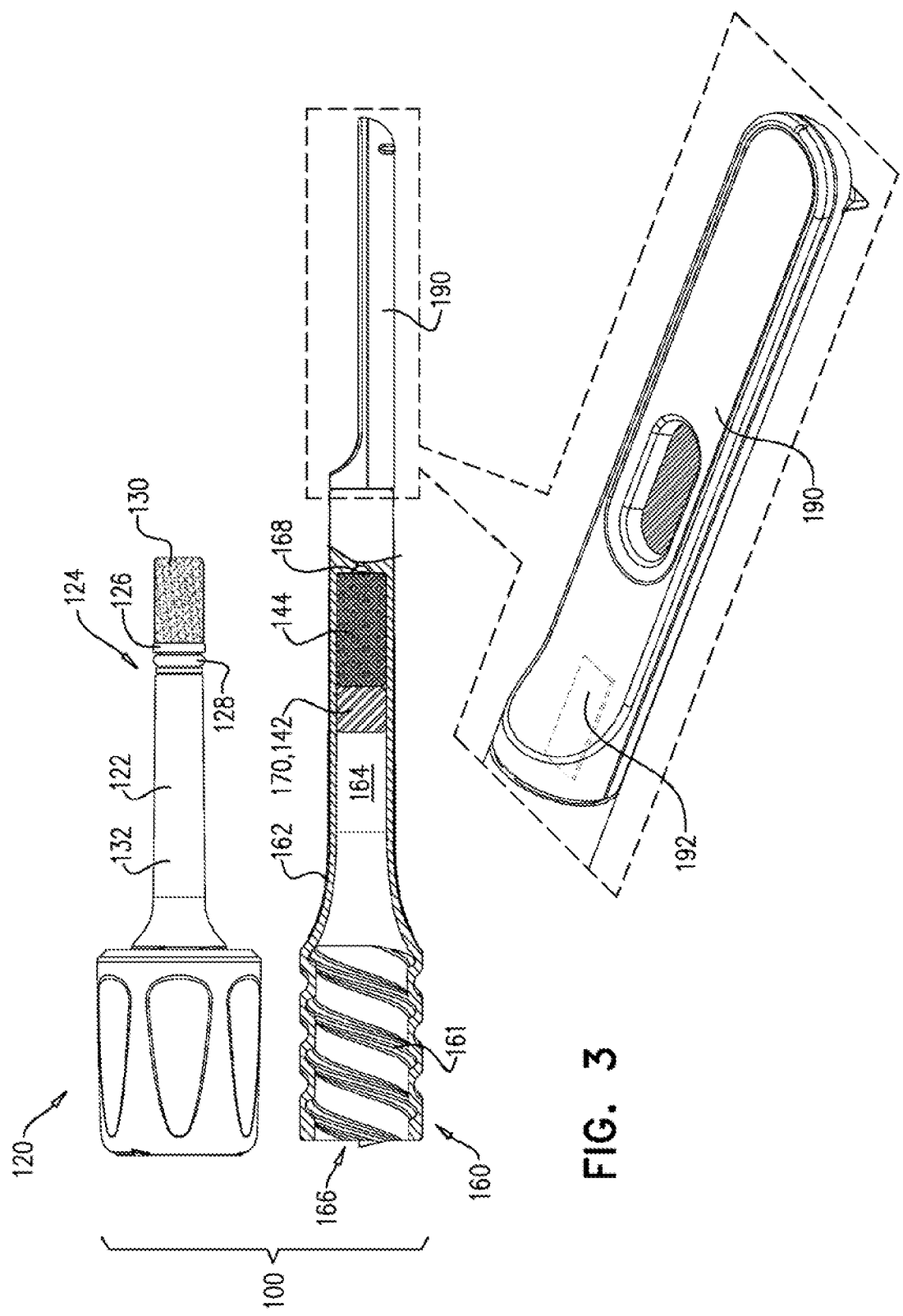

Reference is now made to FIGS. 3 and 4A-B, which are schematic illustrations of a system 100 for use with a body fluid of a subject, in accordance with some applications of the invention. As described hereinabove (e.g., with reference to FIG. 2), for some applications, albumin 42 is mixed and/or dissolved into body fluid 40, and the mixture/solution is introduced into stationary phase 44 —represented by converging arrows 60b and 62b of FIG. 2. System 100 is typically configured to facilitate such a technique, *mutatis mutandis*.

System 100 comprises an elongate barrel 162 and a plunger 122. Typically, plunger 122 is defined by, or is a component of, a first structure 120 of system 100. Typically, barrel 162 is defined by, or is a component of, a second structure 160 of system 100. Each of structures 120 and 160 typically comprises several integrated components, e.g., that are fixed with respect to each other. Typically, structures 120 and 160 are separate from each other (e.g., are provided uncoupled to each other), and are coupled to each other by the user during normal use, as described hereinbelow.

Barrel 162 is shaped to define a channel 164 therethrough, and has an opening 166 into the channel at a proximal region of the barrel, and an outlet 168 from the channel at a distal region of the barrel.

A porous carrier 170 is disposed within channel 164. A cellulosic stationary phase 144 (e.g., comprising cotton and/or CMC) is disposed within channel 164 between carrier 170 and the distal region of the barrel (e.g., between the carrier and outlet 168). A protein, such as an albumin (e.g., BSA) 142 is held in carrier 170, e.g., having been dried therein.

For some applications, stationary phase 144 generally corresponds to stationary phase 44 of FIG. 2. For applications in which stationary phase 144 comprises both cotton and CMC, the stationary phase typically has a cotton:CMC ratio of between 5:1 and 50:1 (e.g., between 10:1 and 25:1). For some applications, albumin 142 generally corresponds to albumin 42 of FIG. 2.

For some applications, and as shown, system 100 (e.g., structure 160) further comprises a lateral flow platform 190, coupled to the distal region of barrel 162 such that the lateral flow platform (e.g., a sample pad 192 thereof) is in fluid communication with outlet 168. Lateral flow platform 190 is configured to detect the analyte of interest (such as an analyte described herein), comprising a lateral flow test comprising antibodies specific to that analyte—e.g., similar to existing lateral flow tests, *mutatis mutandis*.

A distal portion 124 of plunger 122 is introducible into channel 164 via opening 166 (FIG. 4A), and is dimensioned to slide snugly within the channel (FIG. 4B). If a body fluid is disposed within channel 164 proximal from stationary phase 144 and carrier 170, progressive advancement of plunger 122 distally through the channel (i) pushes the body fluid through carrier 170, where the fluid mixes with and/or dissolves albumin 142, (ii) pushes the body fluid and the mixed/dissolved albumin into stationary phase 144, and (iii) pushes the resulting eluate out of the stationary phase, and through outlet 168, e.g., to lateral flow platform 190.

For some applications, movement of the body fluid along channel 164 through carrier 170 and into stationary phase 144 is achieved by advancing plunger 122 (e.g., distal portion 124 thereof) through a first portion of the channel (e.g., a first distance through the channel). For some applications, the eluate is extracted from stationary phase 144 by advancing plunger 122 (e.g., distal portion 124 thereof) through a second portion of channel 164 (e.g., a second distance through the channel). For some such applications, and as described hereinbelow, this applies pressure to (e.g., compresses) the stationary phase, thereby serving as a pressure-applying mechanism for extracting the eluate from the stationary phase.

Typically, and as shown, system 100 (e.g., structure 120 thereof) comprises a sponge 130, coupled to distal portion 124 of plunger 122. For some applications, and as shown, distal portion 124 of plunger 122 defines a crown 126 at a distal end of the plunger, and a piston ring 128, e.g., proximal from the crown. For such applications, sponge 130 is disposed distally from crown 126, e.g., attached to a distal face of the crown.

Sponge 130 is configured to hold a fluid, such as a body fluid 140, and structure 120 (e.g., plunger 122 thereof) is configured to introduce the sponge holding the fluid into channel 164 via opening 166 (FIG. 4A). For some applications, body fluid 140 generally corresponds to body fluid 40 of FIG. 2. Typically, body fluid 140 is introduced into sponge 130 by bathing the sponge in the fluid. For example, for applications in which body fluid 140 is saliva, distal portion 124 of plunger 122 is placed in the mouth of the subject, where it absorbs the saliva. For such applications, sponge 130 is therefore configured to be safe for placement in the mouth of the subject. For example, sponge 130 is securely attached to plunger 122, is non-toxic, and/or is sterile. Typically, sponge 130 contains no additional substances therein that may release and/or dissolve in the mouth of the subject. For some applications, sponge 130 comprises polymeric fibers.

Structure 120 (e.g., plunger 122 thereof) is dimensioned such that sliding of distal portion 124 through channel 164 compresses sponge 130 within the channel (FIG. 4B). To facilitate this, sponge 130 is sufficiently compressible to be compressed by force applied via plunger 122. Compression of sponge 130 holding body fluid 140 drives the body fluid (i) out of the sponge, (ii) through carrier 170, dissolving at least some of albumin 142 disposed therein, (iii) with the dissolved albumin, into stationary phase 144, and (iv) as an eluate, out of the stationary phase and through outlet 168, typically to lateral flow platform 190 (e.g., the sample pad thereof).

Typically, sliding of distal portion 124 of plunger 122 through channel 164 compresses sponge 130 between plunger 122 and carrier 170 (e.g., pressing the sponge against the carrier—i.e., with the sponge in contact with the carrier).

For some applications, the dimensions of structure 120 (e.g., plunger 122 thereof) and the compressibility of carrier 170 are such that sliding of distal portion 124 of the plunger through channel 164 compresses the carrier between sponge 130 and stationary phase 144.

For some applications, structure 120 (e.g., plunger 122 thereof) (i) comprises a screw thread 121 at a proximal portion, configured to couple the plunger to structure 160 (e.g., barrel 162 thereof), and (ii) is dimensioned such that coupling the plunger to the barrel using the screw thread compresses sponge 130 within the channel by sliding distal portion 124 of the plunger through the channel. This is illustrated by the helical arrow in FIG. 4B. For such applications, structure 160 (e.g., barrel 162 thereof) typically comprises a corresponding screw thread 161. Structure 120 (e.g., plunger 122 thereof) typically comprises a stem 132 that extends between screw thread 121 and distal portion 124.

FIG. 4A shows structures 120 and 160 positioned with distal portion 124 of plunger 122 disposed within channel 164 but prior to engagement of screw threads 121 and 161. As shown, in this state, sponge 130 typically remains largely (e.g., completely) uncompressed, e.g., such that compression of the sponge occurs primarily (e.g., only) via screwing of screw threads 121 and 161. Also as shown, in this state, distal portion 124 (e.g., piston ring 128 thereof) is disposed sufficiently distally (i.e., deeply) within channel 164 to have sealed the channel, despite more proximal portions of the channel, closer to opening 166, being typically wider. This therefore prevents inadvertent leakage of the body fluid during subsequent distal advancement of plunger 122.

FIG. 4B shows structures 120 and 160 following complete distal advancement of plunger 122, e.g., by screwing screw thread 121 as far as possible—e.g., until it reaches the end of screw thread 161, and/or until distal portion 124 of the plunger cannot be advanced further distally. As shown, once system 100 is in this state, sponge 130 has become compressed, such that body fluid 140 has been squeezed out of the sponge, and through carrier 170.

For some applications, and as shown, once system 100 is in the state shown in FIG. 4B, carrier 170 has also become compressed (e.g., between sponge 130 and stationary phase 144), thereby facilitating movement of fluid 140 and albumin 142 out of the carrier and through stationary phase 144. That is, for some applications, the dimensions of structure 120 (e.g., plunger 122 thereof) and compressibility of carrier 170 are such that sliding of distal portion 124 of the plunger through channel 164 compresses the carrier between sponge 130 and stationary phase 144.

For some applications, and as shown, once system 100 is in the state shown in FIG. 4B, stationary phase 144 has also become compressed (e.g., between carrier 170 and the distal region of barrel 162, such as between the carrier and outlet 168), thereby facilitating movement of the eluate out of the stationary phase and through outlet 168, e.g., to lateral flow platform 190. That is, for some applications, the dimensions of structure 120 (e.g., plunger 122 thereof) and compressibility of stationary phase 144 are such that sliding of distal portion 124 of the plunger through channel 164 compresses the stationary phase between carrier 170 and the distal region of barrel 162.

For some applications, sponge 130 is more compressible than carrier 170, e.g., such that, before the carrier becomes maximally compressed, the carrier receives at least a portion (e.g., the majority of) of the body fluid that will be extracted from the sponge. For some applications, carrier 170 is more compressible than stationary phase 144, e.g., such that, before the stationary phase becomes maximally compressed, the stationary phase receives at least a portion (e.g., the majority of) of the body fluid that will be extracted from the carrier. In this context, the term "maximally compressed" means as compressed as system 100 is configured to make the element during normal use.

For some applications, system 100 is configured such that carrier 170 is not compressed during normal use.

For some applications, system 100 is configured such that stationary phase 144 is not compressed during normal use.

FIG. 3 shows structures 120 and 160 aligned adjacent to each other in the same degree of advancement as in the state shown in FIG. 4B. A comparison of FIGS. 3 and 4B illustrates that, for some applications, plunger 122 is sufficiently long that, in the state shown in FIG. 4B, distal portion 124 of the plunger (e.g., crown 126) is disposed at a position within channel 164 that, prior to introduction of the plunger into the channel, was occupied by stationary phase 144.

The configuration of system 100 such that the body fluid moves through the system as described hereinabove is typically determined by one or more factors including the capacity and compressibility of sponge 130, carrier 170, and stationary phase 144 relative to each other.

For some applications, system 100 further comprises a polyoxyethylene-polyoxypropylene block copolymer (PPBC), positioned fluidically between carrier 170 and lateral flow platform 190, inclusive. That is, the PPBC is disposed at a site that is at carrier 170, at lateral flow platform 190, or somewhere along the flow path of the body fluid therebetween. For some applications, the PPBC is held in the carrier, e.g., in a dried form, similar to as described hereinabove for the albumin, *mutatis mutandis*. For some applications, the PPBC is held in the lateral flow platform, e.g., on the sample pad thereof. For some applications, the PPBC is held in stationary phase 144.

Figure 13:
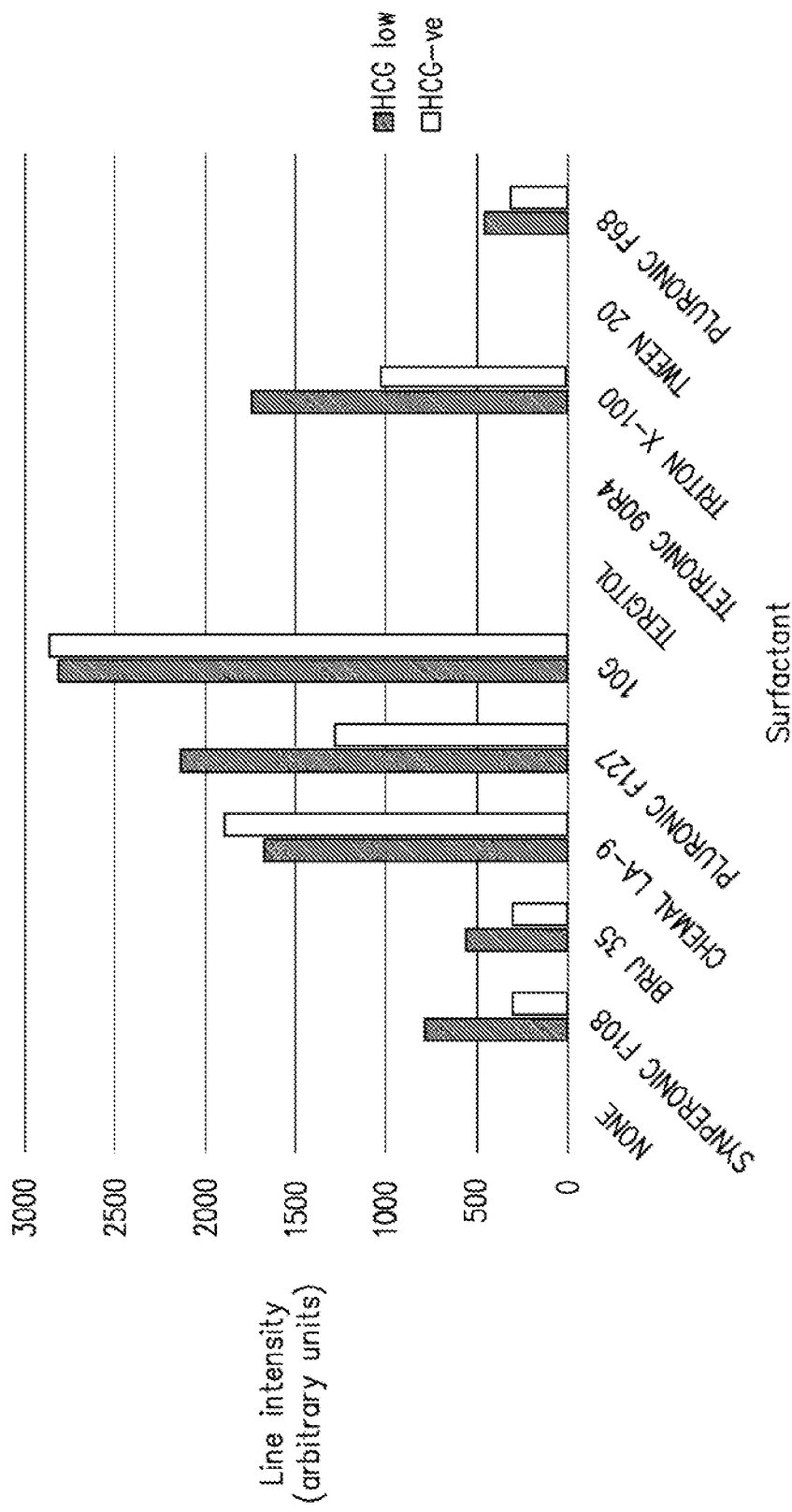

It has been identified by the inventors that inclusion of the PPBC further increases sensitivity and/or reproducibility of the assays performed on the eluate, e.g., the lateral flow test. For some applications, the PPBC is Synperonic(R) F 108 (poly(ethylene glycol)-block-poly(propylene glycol)-block-poly(ethylene glycol)), which the inventors have identified as having a particularly beneficial effect in this regard. Data showing the effect of the PPBC is shown in FIG. 13.

Reference is now made to FIGS. 5, 6, 7, 8, 9, 10, 11, 12, 13, and 14, which show results of various lateral flow test assays, performed on untreated body fluids, or on body fluids treated according to various applications of the invention. In this context, a "treated" body fluid means the eluate derived from treating the body fluid according to an application of the invention.

Figure 5:

FIG. 5 shows the results of lateral flow tests for HCG, performed on one of two body fluids: saliva or urine. The lateral flow test was a commercial pregnancy test originally intended for use with a urine sample. The results are shown as photographs of the respective test window.

The samples were taken from healthy male subjects, and therefore naturally do not contain HCG. Recombinant beta-HCG was added to the samples, to a final concentration of 10 mIU. A control was provided, to which beta-HCG was not added. The samples to which beta-HCG was added were either otherwise untreated, or were treated according to an application of the current invention, in which the fluid was introduced to the stationary phase, an albumin-containing eluent was subsequently introduced to the stationary phase, and an eluate was obtained. The control was treated according to the same application of the invention.

HCG was detected in untreated urine, and this positive result was enhanced in treated urine. HCG was not detected in untreated saliva, but was detected in treated saliva. No false positive result was seen for the control samples. Therefore, treatment of body fluid in accordance with an application of the invention enhances detection of an analyte in that body fluid.

Figure 6:
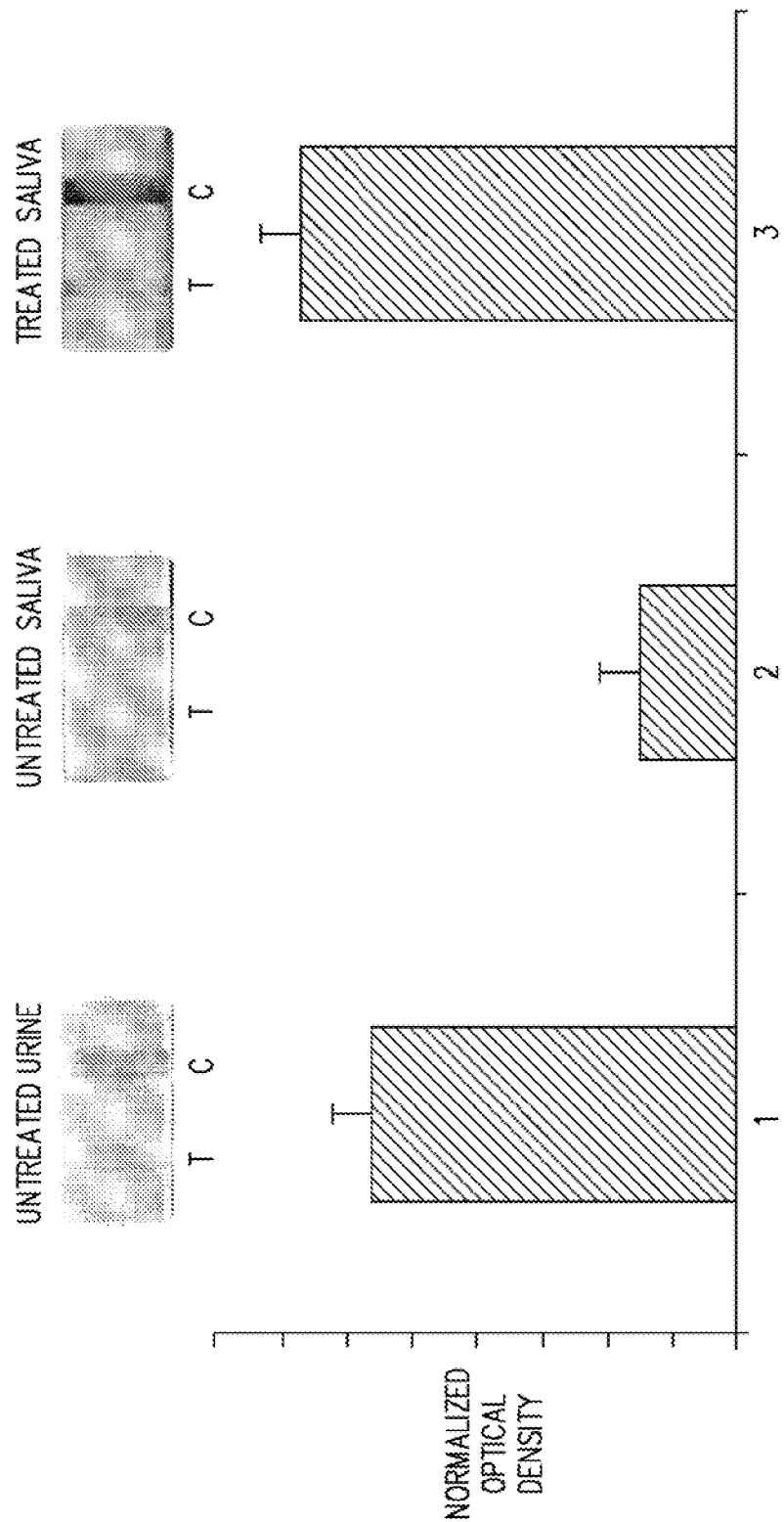

FIG. 6 shows the results of lateral flow tests for luteinizing hormone (LH), performed on one of two body fluids: saliva or urine. The lateral flow test was a commercial ovulation test originally intended for use with a urine sample. The results are shown as photographs of the respective test window, as well as a semi-quantitative measurement of normalized optical density (arbitrary units).

The samples were taken from healthy female subjects during their ovulation period, during which the subjects naturally increase LH expression.

A positive result (a visible test line) was obtained from untreated urine. A negative result (no visible test line) was obtained from untreated saliva. However, a positive result was obtained from saliva treated according to an application of the current invention, in which the saliva was introduced to the stationary phase, an albumin-containing eluent was subsequently introduced to the stationary phase, and an eluate was obtained. Therefore, treatment of body fluid in accordance with at least one application of the invention enhances detection of an analyte in that body fluid.

FIG. 7 shows the results of lateral flow tests for malaria, performed on saliva. The lateral flow test was a commercial malaria test originally intended for detecting HRP II in a blood sample. The results are shown as photographs of the respective test window.

The samples were taken from malaria patients, and were either left untreated, or were treated in accordance with an application of the invention, in which the fluid was introduced to the stationary phase, an albumin-containing eluent was subsequently introduced to the stationary phase, and an eluate was obtained.

A negative result (no visible test line) was obtained from untreated saliva. However, a positive result (a visible test line) was obtained from treated saliva. Therefore, treatment of body fluid in accordance with at least one application of the invention enhances detection of an analyte in that body fluid.

FIG. 8 shows the results of lateral flow tests for *H. pylori*, performed on saliva. The lateral flow test was a commercial *H. pylori* test originally intended for detecting *H. pylori* in a fecal sample. The results are shown as photographs of the respective test window.

The samples were taken from healthy subjects, and an inactivated *H. pylori* lysate was added to the samples to simulate *H. pylori* infection. Samples were either left untreated, or were treated in accordance with an application of the invention, in which the fluid was introduced to the stationary phase, an albumin-containing eluent was subsequently introduced to the stationary phase, and an eluate was obtained.

A negative result (no visible test line) was obtained from untreated saliva. However, a positive result (a visible test line) was obtained from treated saliva. Therefore, treatment of body fluid in accordance with at least one application of the invention enhances detection of an analyte in that body fluid.

FIG. 9 shows the results of lateral flow tests for *C. albicans*, performed on saliva. The lateral flow test was a commercial *Candida* test originally intended for detecting *Candida* in a vaginal sample. The results are shown as photographs of the respective test window.

The samples were taken from healthy subjects, and *Candida* cells were added to the samples to a final concentration of 50,000 cells/ml to simulate *Candida* infection. Samples were either left untreated, or were treated in accordance with an application of the invention, in which the fluid was introduced to the stationary phase, an albumin-containing eluent was subsequently introduced to the stationary phase, and an eluate was obtained.

A negative result (no visible test line) was obtained from untreated saliva. However, a positive result (a visible test line) was obtained from treated saliva. Therefore, treatment of body fluid in accordance with at least one application of the invention enhances detection of an analyte in that body fluid.

FIG. 10 shows the results of lateral flow tests for THC, performed on saliva. The lateral flow test was part of a commercial multipanel test, and was originally intended for detecting THC in a saliva sample. This particular test is a competition assay—discussed below. The results are shown as photographs of the respective test window.

The samples were taken from healthy subjects, and THC was added to the samples to a final concentration of 25 ng/ml. Samples were either left untreated, or were treated in accordance with an application of the invention, in which the fluid was introduced to the stationary phase, an albumin-containing eluent was subsequently introduced to the stationary phase, and an eluate was obtained.

A negative result was obtained from untreated saliva. (Because this test is a competition assay, the presence of a test line represents a negative result). However, a positive result was obtained from treated saliva. (Because this test is a competition assay, the absence of a test line represents a positive result). Therefore, treatment of body fluid in accordance with at least one application of the invention enhances detection of an analyte in that body fluid.

Figure 11:
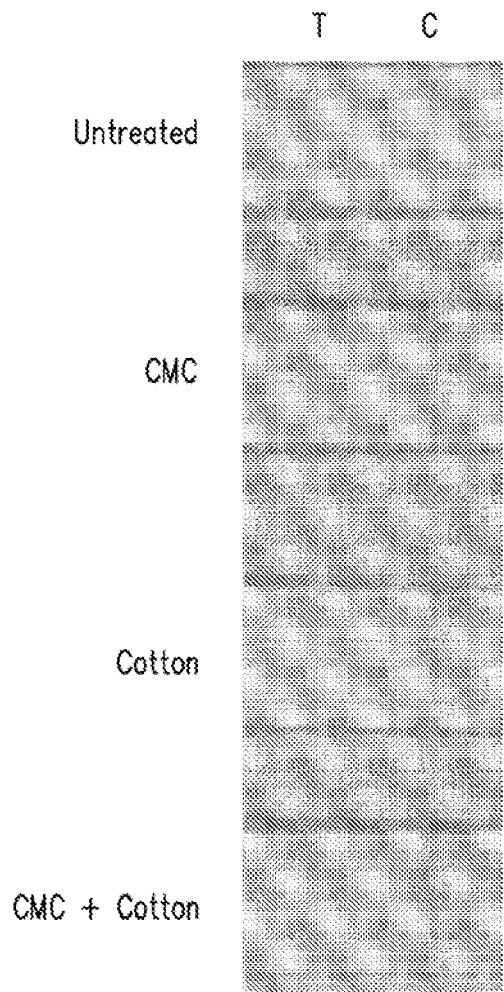
Figure 12:
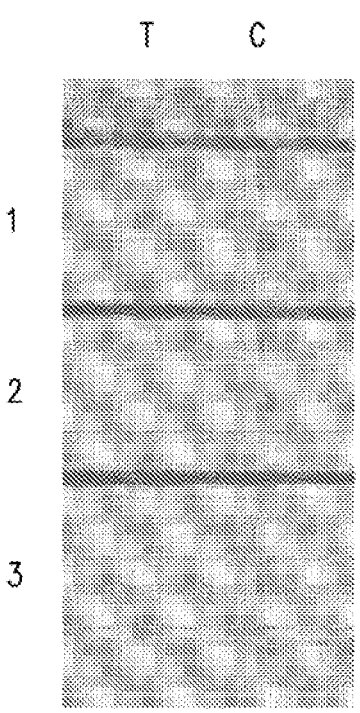

FIGS. 11-12 show results of lateral flow tests for HCG using saliva that either was untreated, or was treated in accordance with an application of the invention, e.g., as described with reference to FIGS. 1-2, *mutatis mutandis*. More specifically, different cellulosic stationary phases were used. The saliva used was from healthy female subjects in early pregnancy (0-1 days after a missed period), and therefore contained HCG, albeit at a low level.

FIG. 11 shows that saliva, not treated in accordance with an application of the invention, did not generate a visible test line or a control line. FIG. 11 also shows that treatment of the saliva in accordance with an application of the invention did result in a visible control line and a visible test line, whether the stationary phase that was used comprised CMC, cotton, or a combination thereof.

FIG. 12 shows results from saliva, treated in accordance with an application of the invention, whereby the stationary phase comprised a commercially-available dental roll, comprising cellulosic fibers. Strip 1 shows the result from saliva that had been treated in accordance with an application of the invention in which the stationary phase used was Roeko Luna dental roll from Coltene/Whaledent GmbH (Germany). Strip 2 shows the result from HCG-containing saliva that had been treated in accordance with an application of the invention in which the stationary phase used was dental cotton roll from Naot Medical (Israel), containing 99.5 percent cotton, and 0.5 percent CMC. Strip 3 shows the result from HCG-containing saliva that had been treated in accordance with an application of the invention in which the stationary phase used was dental cotton roll from DENTaccess (Israel), containing 99.5 percent cotton, and 0.5 percent croscarmellose sodium (an internally cross-linked sodium carboxymethylcellulose). As shown, in each of these cases, control and test lines were visible.

FIG. 13 shows results from results of lateral flow tests for HCG using saliva that was treated in accordance with an application of the invention, e.g., as described with reference to FIGS. 1-2, *mutatis mutandis*. More specifically, the experiments that generated the data in FIG. 13 were performed using system 100, *mutatis mutandis*.

Various surfactants were added to the saliva, to a concentration of 0.5%, and a negative control received no surfactant. For each surfactant, a negative control saliva that did not contain HCG was compared with saliva containing a low concentration of HCG. The HCG-negative saliva was obtained from healthy subjects who were known not to be pregnant. The HCG-low saliva was obtained from health subjects in early pregnancy (0-1 days after a missed period), and therefore contained HCG, albeit at a low level. The intensity of the test line of each lateral flow test was semi-quantitively measured using a reflectance reader (Axxin, Australia).

The absence of bars for no surfactant, Tergitol, and Tetronic 90R4 is due to poor visualization on the test strips, resulting from poor flow characteristics. The test line intensity for these test strips was not measured. In addition to good flow characteristics, it is desirable that assay 50 (e.g., a lateral flow test) provides a visible test line for samples that contain the analyte (sensitivity) but not for samples that do not contain the analyte (false positives). Although several of the surfactants tested provided a test line for the HCG-containing saliva that was more intense than corresponding test line for the HCG-negative saliva, the intensity of the test line for the HCG-negative saliva was nonetheless higher than the inventors deem optimal. Synperonic(R) F 108, Brij(R) 35 (polyethylene glycol dodecyl ether), and Pluronic (R) F 68 (polyoxyethylene-polyoxypropylene block copolymer) resulted in advantageously low-intensity test lines for the HCG-negative saliva, and advantageously higher-intensity test lines for the HCG-containing saliva. Of these, Synperonic(R) F 108 provided the most intense test line for the HCG-containing saliva. Therefore, as described hereinabove, for some applications Synperonic(R) F 108 (poly (ethylene glycol)-block-poly(propylene glycol)-block-poly (ethylene glycol)), is introduced prior to analysis 50.

Figure 14:
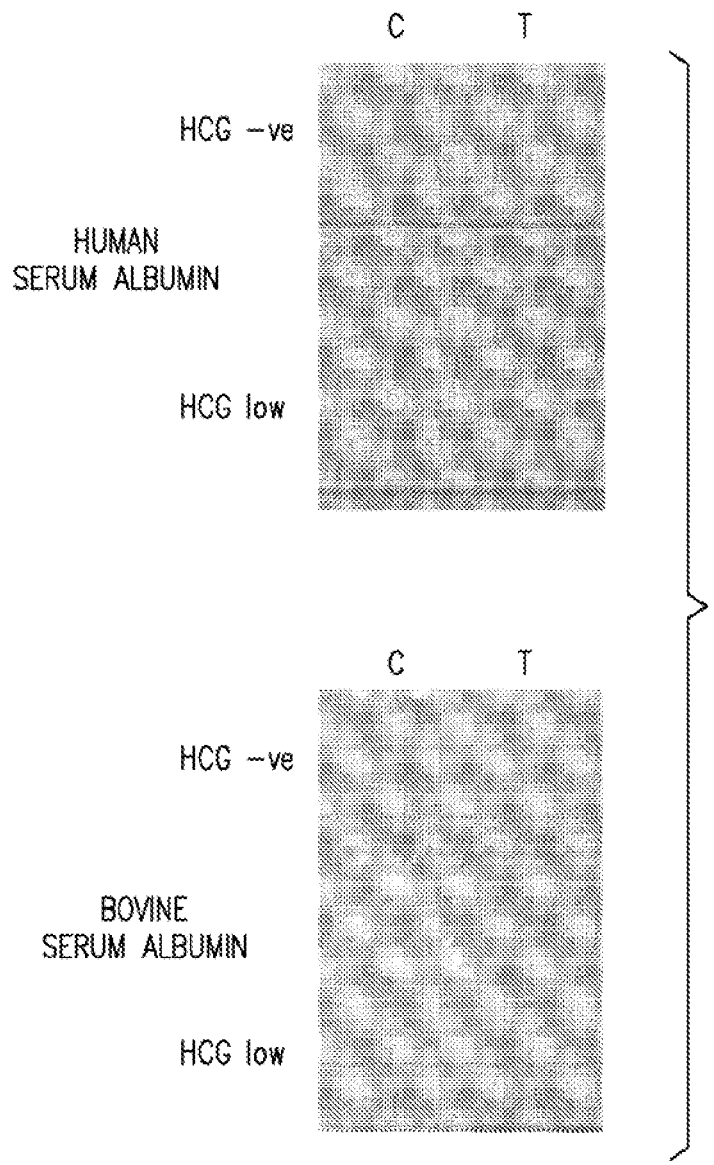

FIG. 14 shows results of lateral flow tests for HCG using saliva that was treated in accordance with an application of the invention, e.g., as described with reference to FIGS. 1-2, *mutatis mutandis*. More specifically, different albumins were used: human serum albumin (HSA) and bovine serum albumin (BSA). For each albumin, a negative control saliva that did not contain HCG was compared with saliva containing a low concentration of HCG. The HCG-negative saliva was obtained from healthy subjects who were known not to be pregnant. The HCG-low saliva was obtained from healthy female subjects in early pregnancy (0-1 days after a missed period), and therefore contained HCG, albeit at a low level.

FIG. 14 shows that the HCG-negative saliva did not result in a visible test line, whether HSA or BSA was used. FIG. 14 also shows that, whichever of the albumins was used, the HCG-low saliva resulted in a visible test line. All of the tests had visible control lines.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    an elongate barrel, shaped to define a channel therethrough, the barrel having:
        an opening into the channel at a proximal region of the barrel, and
        an outlet from the channel at a distal region of the barrel,
        wherein the channel has a longitudinal axis extending from the opening of the barrel to the outlet of the barrel;
    a porous carrier, disposed within the channel along the axis;
    a protein, held in the carrier, the protein being an albumin;
    a cellulosic stationary phase, disposed within the channel along the axis between the carrier and the distal region of the barrel;
    a lateral flow platform, coupled to the distal region of the barrel such that a sample pad of the lateral flow platform is in fluid communication with the outlet;
    a plunger, having a distal portion that is introducible into the channel via the opening, and is dimensioned to slide snugly within the channel along the axis; and
    a sponge, coupled to the distal portion of the plunger, and configured to hold saliva,
    wherein the plunger is:
        configured to introduce the sponge holding the saliva into the channel via the opening, and
        dimensioned such that sliding of the distal portion through the channel along the axis compresses the sponge, the carrier and the stationary phase within the channel, and wherein the apparatus is configured such that, while the sponge holds the saliva, compression of the sponge within the channel drives the saliva along the axis:
        out of the compressed sponge and through the compressed carrier, dissolving at least some of the albumin,
        out of the compressed carrier, and with the dissolved albumin, through the compressed stationary phase, and
        as an eluate, out of the compressed stationary phase, through the outlet, and then onto the sample pad of the lateral flow platform.

2. The apparatus according to claim 1, wherein the stationary phase comprises cellulosic fibers.

3. The apparatus according to claim 1, wherein the stationary phase comprises cotton.

4. The apparatus according to claim 1, wherein the stationary phase comprises carboxymethyl cellulose (CMC).

5. The apparatus according to claim 1, wherein the lateral flow platform comprises a human chorionic gonadotropin (HCG) lateral flow test comprising antibodies specific to HCG.

6. The apparatus according to claim 1, wherein the lateral flow platform comprises a *Plasmodium* flow test comprising antibodies specific to histidine-rich protein 2 (HRPII).

7. The apparatus according to claim 1, wherein the lateral flow platform comprises a *Plasmodium* flow test comprising antibodies specific to pan-*Plasmodium* antigen lactate dehydrogenase (pLDH).

8. The apparatus according to claim 1, wherein the lateral flow platform comprises a luteinizing hormone (LH) flow test comprising antibodies specific to LH.

9. The apparatus according to claim 1, wherein the lateral flow platform comprises a *Helicobacter pylori* flow test comprising antibodies specific to a *Helicobacter pylori* antigen.

10. The apparatus according to claim 1, wherein the lateral flow platform comprises a *Candida* flow test comprising antibodies specific to a *Candida* spp. antigen.

11. The apparatus according to claim 1, wherein the lateral flow platform comprises a tetrahydrocannabinol (THC) flow test comprising antibodies specific to THC.

12. The apparatus according to claim 1, wherein the albumin is bovine serum albumin.

13. The apparatus according to claim 1, wherein the albumin is dried.

14. The apparatus according to claim 1, further comprising a polyoxyethylene-polyoxypropylene block copolymer, positioned fluidically between the carrier and the lateral flow platform, inclusive.

15. The apparatus according to claim 14, wherein the polyoxyethylene-polyoxypropylene block copolymer is held in the carrier.

16. The apparatus according to claim 14, wherein the polyoxyethylene-polyoxypropylene block copolymer is held in the lateral flow platform.

17. The apparatus according to claim 14, wherein the polyoxyethylene-polyoxypropylene block copolymer is held in the stationary phase.

18. The apparatus according to claim 14, wherein the polyoxyethylene-polyoxypropylene block copolymer is poly(ethylene glycol)-block-poly(propylene glycol)-block-poly(ethylene glycol).

19. The apparatus according to claim 1, wherein the carrier is sufficiently compressible, and the plunger is dimensioned, such that sliding of the distal portion of the plunger through the channel along the axis compresses the carrier between the sponge and the stationary phase.

20. The apparatus according to claim 1, wherein the plunger is dimensioned such that the sliding of the distal portion through the channel along the axis compresses the sponge between the plunger and the carrier.

21. The apparatus according to claim 1, wherein the plunger:
has a proximal portion that comprises a screw thread, configured to couple the plunger to the barrel;
comprises a stem that extends between the screw thread and the distal portion; and
is dimensioned such that coupling the plunger to the barrel using the screw thread compresses the sponge within the channel by sliding the distal portion through the channel along the axis.

22. The apparatus according to claim 21, wherein the plunger is dimensioned such that coupling the plunger to the barrel using the screw thread compresses the carrier between the sponge and the stationary phase by sliding the distal portion through the channel along the axis.

23. The apparatus according to claim 1, further comprising a surfactant, positioned fluidically between the carrier and the lateral flow platform, inclusive.

24. The apparatus according to claim 23, wherein the surfactant is held in the carrier.

25. The apparatus according to claim 23, wherein the surfactant is held in the lateral flow platform.

26. The apparatus according to claim 23, wherein the surfactant is held in the stationary phase.

27. Apparatus, comprising:
an elongate barrel, shaped to define a channel therethrough, the barrel having:
an opening into the channel at a proximal region of the barrel, and
an outlet from the channel at a distal region of the barrel,
wherein the channel has a longitudinal axis extending from the opening of the barrel to the outlet of the barrel;
a porous carrier, disposed within the channel along the axis;
a surfactant, held in the carrier;
a lateral flow platform, coupled to the distal region of the barrel such that a sample pad of the lateral flow platform is in fluid communication with the outlet;
a plunger, having a distal portion that is introducible into the channel via the opening, and is dimensioned to slide snugly within the channel along the axis; and
a sponge, coupled to the distal portion of the plunger, and configured to hold saliva,
wherein the plunger is:
configured to introduce the sponge holding the saliva into the channel via the opening, and
dimensioned such that sliding of the distal portion through the channel along the axis compresses the sponge and the carrier within the channel, and wherein the apparatus is configured such that, while the sponge holds the saliva, compression of the sponge within the channel drives the saliva along the axis:
out of the compressed sponge and through the compressed carrier, dissolving at least some of the surfactant, and
out of the compressed carrier, with the dissolved surfactant, through the outlet, and then onto the sample pad of the lateral flow platform.

28. The apparatus according to claim 27, wherein the lateral flow platform comprises a human chorionic gonadotropin (HCG) lateral flow test comprising antibodies specific to HCG.

29. The apparatus according to claim 27, wherein the lateral flow platform comprises a *Plasmodium* flow test comprising antibodies specific to histidine-rich protein 2 (HRPII).

30. The apparatus according to claim 27, wherein the lateral flow platform comprises a *Plasmodium* flow test comprising antibodies specific to pan-*Plasmodium* antigen lactate dehydrogenase (pLDH).

31. The apparatus according to claim 27, wherein the lateral flow platform comprises a luteinizing hormone (LH) flow test comprising antibodies specific to LH.

32. The apparatus according to claim 27, wherein the lateral flow platform comprises a *Helicobacter pylori* flow test comprising antibodies specific to a *Helicobacter pylori* antigen.

33. The apparatus according to claim 27, wherein the lateral flow platform comprises a *Candida* flow test comprising antibodies specific to a *Candida* spp. antigen.

34. The apparatus according to claim 27, wherein the lateral flow platform comprises a tetrahydrocannabinol (THC) flow test comprising antibodies specific to THC.

35. The apparatus according to claim 27, wherein the carrier is sufficiently compressible, and the plunger is dimensioned, such that sliding of the distal portion of the plunger through the channel along the axis compresses the carrier between the sponge and the outlet.

36. The apparatus according to claim 27, wherein the plunger is dimensioned such that the sliding of the distal portion through the channel along the axis compresses the sponge between the plunger and the carrier.

37. The apparatus according to claim 27, wherein the plunger:
  has a proximal portion that comprises a screw thread, configured to couple the plunger to the barrel;
  comprises a stem that extends between the screw thread and the distal portion; and
  is dimensioned such that coupling the plunger to the barrel using the screw thread compresses the sponge within the channel by sliding the distal portion through the channel along the axis.

38. The apparatus according to claim 37, wherein the plunger is dimensioned such that coupling the plunger to the barrel using the screw thread compresses the carrier between the sponge and the outlet by sliding the distal portion through the channel along the axis.

39. Apparatus, comprising:
  a plunger;
  an elongate barrel, shaped to define a channel therethrough, the barrel having:
    an opening into the channel at a proximal region of the barrel, and
    an outlet from the channel at a distal region of the barrel, the outlet having a cross-sectional area that is smaller than a cross-sectional area of the plunger,
    wherein the channel has a longitudinal axis extending from the opening of the barrel to the outlet of the barrel;
  a porous carrier, disposed within the channel along the axis;
  a protein, held in the carrier, the protein being an albumin;
  a cellulosic stationary phase, disposed within the channel along the axis between the carrier and the distal region of the barrel;
  a lateral flow platform, coupled to the distal region of the barrel such that a sample pad of the lateral flow platform is in fluid communication with the outlet; and
  a sponge, coupled to the distal portion of the plunger, and configured to hold saliva,
wherein the plunger has a distal portion that is introducible into the channel via the opening, and the plunger is:
  configured to introduce the sponge holding the saliva into the channel via the opening, and
  dimensioned to slide snugly within the channel along the axis, such that sliding of the distal portion through the channel along the axis compresses the sponge within the channel, and
wherein the apparatus is configured such that, while the sponge holds the saliva, compression of the sponge within the channel drives the saliva along the axis:
  out of the sponge and through the carrier, dissolving at least some of the albumin,
  with the dissolved albumin, into the stationary phase, and
  as an eluate, out of the stationary phase, through the outlet, and then onto the sample pad of the lateral flow platform.

40. The apparatus according to claim 39, wherein a distal wall of the barrel is shaped to define the outlet.

41. Apparatus, comprising:
  a plunger;
  an elongate barrel, shaped to define a channel therethrough, the barrel having:
    an opening into the channel at a proximal region of the barrel, and
    an outlet from the channel at a distal region of the barrel, the outlet having a cross-sectional area that is smaller than a cross-sectional area of the plunger,
    wherein the channel has a longitudinal axis extending from the opening of the barrel to the outlet of the barrel;
  a porous carrier, disposed within the channel along the axis;
  a surfactant, held in the carrier;
  a lateral flow platform, coupled to the distal region of the barrel such that a sample pad of the lateral flow platform is in fluid communication with the outlet; and
  a sponge, coupled to the distal portion of the plunger, and configured to hold saliva,
wherein the plunger has a distal portion that is introducible into the channel via the opening, and the plunger is:
  configured to introduce the sponge holding the saliva into the channel via the opening, and
  dimensioned to slide snugly within the channel along the axis, such that sliding of the distal portion through the channel along the axis compresses the sponge within the channel, and
wherein the apparatus is configured such that, while the sponge holds the saliva, compression of the sponge within the channel drives the saliva along the axis:
  out of the sponge and through the carrier, dissolving at least some of the surfactant,
  with the dissolved surfactant, through the outlet, and then onto the sample pad of the lateral flow platform.

42. The apparatus according to claim 41, wherein a distal wall of the barrel is shaped to define the outlet.

* * * * *